(12) United States Patent
Kayed

(10) Patent No.: US 10,266,585 B2
(45) Date of Patent: Apr. 23, 2019

(54) METHODS OF TREATING BRAIN INJURY

(71) Applicant: Rakez Kayed, Galveston, TX (US)

(72) Inventor: Rakez Kayed, Galveston, TX (US)

(73) Assignee: THE BOARD OF REGENTS OF THE UNIVERITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/324,289

(22) Filed: Jul. 7, 2014

(65) Prior Publication Data

US 2015/0004169 A1 Jan. 1, 2015

Related U.S. Application Data

(63) Continuation-in-part of application No. 13/393,220, filed on Oct. 1, 2012, now Pat. No. 8,778,343, which is a continuation-in-part of application No. 13/273,507, filed as application No. PCT/US2010/047154 on Aug. 30, 2010, now Pat. No. 9,125,846.

(60) Provisional application No. 61/886,141, filed on Oct. 3, 2013, provisional application No. 61/393,685, filed on Oct. 15, 2010, provisional application No. 61/237,861, filed on Aug. 28, 2009.

(51) Int. Cl.
  *C07K 16/18* (2006.01)
  *G01N 33/68* (2006.01)

(52) U.S. Cl.
  CPC ......... *C07K 16/18* (2013.01); *G01N 33/6896* (2013.01); *C07K 2317/33* (2013.01); *G01N 2800/2821* (2013.01)

(58) Field of Classification Search
  CPC ............. A61K 2039/505; C07K 16/18; G01N 2800/28
  See application file for complete search history.

(56) References Cited

U.S. PATENT DOCUMENTS

| | | | |
|---|---|---|---|
| 4,338,298 A | 7/1982 | Myers | |
| 4,554,101 A | 11/1985 | Hopp | |
| 4,748,018 A | 5/1988 | Stolle et al. | |
| 5,512,282 A | 4/1996 | Krivan et al. | |
| 5,548,066 A | 8/1996 | Leneau et al. | |
| 5,693,762 A | 12/1997 | Queen et al. | |
| 6,651,655 B1 | 11/2003 | Licalsi et al. | |
| 6,756,361 B1 | 6/2004 | Fattom et al. | |
| 6,770,278 B1 | 8/2004 | Skelly | |
| 6,936,258 B1 | 8/2005 | Pavliak et al. | |
| 7,439,041 B2 | 10/2008 | Michelitsch et al. | |
| 2004/0005643 A1 | 1/2004 | De Santis et al. | |
| 2004/0137421 A1 | 7/2004 | Kitamoto et al. | |
| 2007/0218491 A1 | 9/2007 | Vasan et al. | |
| 2008/0050383 A1 | 2/2008 | Sigurdsson et al. | |
| 2008/0220449 A1 | 9/2008 | Vasan et al. | |
| 2009/0075984 A1 | 3/2009 | Wischik et al. | |
| 2009/0123936 A1 | 5/2009 | Novak | |
| 2009/0162336 A1 | 6/2009 | Mandelkow et al. | |
| 2009/0258009 A1 | 10/2009 | Gellerfors et al. | |
| 2010/0209422 A1 | 8/2010 | Ravetch et al. | |
| 2011/0052608 A1 | 3/2011 | Head et al. | |
| 2012/0198573 A1* | 8/2012 | Roberson ........... | G01N 33/5023 800/3 |
| 2012/0276009 A1* | 11/2012 | Pfeifer ............... | A61K 39/0005 424/9.1 |
| 2012/0301473 A1* | 11/2012 | Binder ............... | C07K 14/4711 424/139.1 |
| 2014/0234214 A1* | 8/2014 | Griswold-Prenner ..................... | C07K 16/18 424/1.49 |
| 2017/0273963 A1* | 9/2017 | Gestwicki ............ | C07D 417/14 |

FOREIGN PATENT DOCUMENTS

| | | | |
|---|---|---|---|
| WO | 00/29850 | 5/2000 | |
| WO | 2004/024090 | 3/2004 | |
| WO | 2005/061544 | 7/2005 | |
| WO | 2005/061545 | 7/2005 | |
| WO | 2008/028939 | 3/2008 | |
| WO | WO/2011026031 | * 3/2011 | ........... A61K 39/395 |
| WO | 2011/038575 | 4/2011 | |

OTHER PUBLICATIONS

McKee 2009 "chronic traumatic encephalopathy in athletes: progressive tauopathy following repetitive head injury" J neuropathol Exp Neurol 68(7):709-735.*
Ren 2013 "Characteristics of tau oligomers" Frontiers in neurology 4:102.*
Rubenstein 2012 "Traumatic brain injury: risk factors and biomarkers of Alzheimer's disease and chronic traumatic encephalopathy" Curr Tran Geriatr Gerontol Rep 1:143-148.*
Liliang 2010 ".tau. proteins in serum predict outsome after severe traumatic brain injury" J Surgical research 160:302-307.*
Stocchetti 2015 "neuroprotection in acute brain injury: an up-to-date review" critical care 19:186.*
Tran 2011 "The association between traumatic brain injury and alzheimer's disease: mouse models and potential mechanisms" ETDs 651 (Year: 2011).*
Tran 2011b "Distinct Temporal and Anatomical Distributions of Amyloid-b and Tau Abnormalities following Controlled Cortical Impact in Transgenic Mice" plos one 6(9):e25475 (Year: 2011).*
Hoshino "Emergence of immunoreactivities for phosphorylated tau and amyloid-b protein in chronic stage of fluid percussion injury in rat brain" rapid science ltd 9(8):1879-1883 (Year: 1998).*

(Continued)

*Primary Examiner* — Adam Weidner
(74) *Attorney, Agent, or Firm* — Norton Rose Fulbright US LLP

(57) ABSTRACT

Embodiments of the invention are directed to compositions and methods related to Tau oligomers and Tau oligomer specific antibodies and their use in detecting and/or treating traumatic brain injury or chronic traumatic encephalopathy.

9 Claims, 15 Drawing Sheets

Specification includes a Sequence Listing.

(56) References Cited

OTHER PUBLICATIONS

Mouzon "Repetitive Mild Traumatic Brain Injury in a Mouse Model Produces Learning and Memory Deficits Accompanied by Histological Changes" J neurotrauma 29:2761-2773 (Year: 2012).*
Chen "Enhancement and destruction of antibody function by somatic mutation: unequal occurrence is controlled by V gene combinatorial associations" EMBO Journal vol. 14 No. 1 2 pp. 2784-2794 (Year: 1995).*
Kussie "A Single Engineered Amino Acid Substitution Changes Antibody Fine Specificity" J immunol 152(1):146-52 (Year: 1994).*
Extended Search Report for EP 10812710.1 dated Mar. 7, 2013.
Extended Search Report for EP 11833463.0 dated Feb. 13, 2014.
International Preliminary Report on Patentability for PCT/US2010/047154 dated Feb. 28, 2012.
International Search Report for PCT/US2010/047154 dated Dec. 21, 2010.
International Preliminary Report on Patentability for PCT/US2011/056293 dated Apr. 16, 2013.
International Search Report for PCT/US2011/056293 dated Apr. 9, 2012.
Alafuzoff et al., "Staging of Neurofibrillary Pathology in Alzheimer's Disease: A Study of the BrainNet Europe Consortium," Brain Pathology, vol. 18, 2008, pp. 484-496.
Alonso et al., "Mechanism of tau-induced neurodegeneration in Alzheimer disease and related tauopathies," Curr. Alzheimer Res., vol. 5, No. 4, 2008, pp. 375-384.
Andreasen et al., "Cerebrospinal fluid tau and Aβ42 as predictors of development of Alzheimer's disease in patients with mild cognitive impairment," Neuroscience Letters, vol. 273, 1999, pp. 5-8.
Asuni et al., "Immunotherapy Targeting Pathological Tau Conformers in a Tangle Mouse Model Reduces Brain Pathology with Associated Functional Improvements," The Journal of Neuroscience, vol. 37, No. 34, 2007, pp. 9115-9129.
Augustinack et al., "Specific tau phosphorylation sites correlate with severity of neuronal cytopathology in Alzheimer's disease," Acta Neuropathol., vol. 103, 2002, pp. 26-35.
Avila et al., "Assembly In Vitro of Tau Protein and its Implications in Alzheimer's Disease," Current Alzheimer Research, vol. 1, 2004, pp. 97-101.
Ballatore et al., "Tau-mediated neurodegeneration in Alzheimer's disease and related disorders," Neuroscience, vol. 8, 2007, pp. 663-672.
Barrantes et al., "Tau Aggregation Followed by Atomic Force Microscopy and Surface Plasmon Resonance, and Single Molecule Tau-Tau Interaction Probed by Atomic Force Spectroscopy," Journal of Alzheimer's Disease, vol. 18, 2009, pp. 141-151.
Berger et al., "Accumulation of Pathological Tau Species and Memory Loss in a Conditional Model of Tauopathy," The Journal of Neuroscience, vol. 27, No. 14, 2007, pp. 3650-3662.
Blom et al., "Rapid progression from mild cognitive impairment to Alzheimer's disease in subjects with elevated levels of tau in cerebrospinal fluid and the APOE epsilon4/epsilon4 genotype," Dement. Geriatr. Cogn. Disord., vol. 27, No. 5, 2009, pp. 458-464.
Bondareff et al., "Immunohistochemical Staging of Neurofibrillary Degeneration in Alzheimer's Disease," Journal of Neuropathology and Experimental Neurology, vol. 53, No. 2, 1994, pp. 158-164.
Borroni et al., "Predicting Alzheimer dementia in mild cognitive impairment patients: Are biomarkers useful?" European Journal of Pharmacology, vol. 545, 2006, pp. 73-80.
Braak et al., "Demonstration of Amyloid Deposits and Neurofibrillary Changes in Whole Brain Sections," Brain Pathology, vol. 1, No. 3, 1991, pp. 213-216.
Braak et al., "Neuropathological staging of Alzheimer-related changes," Acta Neuropathologica, vol. 82, No. 4, 1991, pp. 239-259.
Braak et al., "Evolution of the neuropathology of Alzheimer's disease," Acta Neurol. Scand., Suppl. 165, 1996, pp. 3-12.
Bretteville et al., "Tau Aggregates: Toxic, Inter, or Protective Species?" Journal of Alzheimer's Disease, vol. 14, 2008, pp. 431-436.

Brunden et al., "Evidence That Non-Fibrillar Tau Causes Pathology Linked to Neurodegeneration and Behavioral Impairments," J. Alzheimers Dis., vol. 14, No. 4, 2008, pp. 393-399.
Buerger et al., "CSF phosphorylated tau protein correlates with neocortical neurofibrillary pathology in Alzheimer's disease," Brain, vol. 129, 2006, pp. 3035-3041.
Busciglio et al., β-Amyloid Fibrils Induce Tau Phosphorylation and Loss of Microtubule Binding, Neuron, vol. 14, 1995, pp. 879-888.
Cardinale et al., "The potential of intracellular antibodies for therapeutic targeting of protein-misfolding diseases," Trends in Molecular Medicine, vol. 14, No. 9, 2008, pp. 373-380.
Congdon et al., "Is Tau Aggregation Toxic or Protective?" Journal of Alzheimer's Disease, vol. 14, 2008, pp. 453-457.
De Felice et al., "Alzheimer's disease-type neuronal tau hyperphosphorylation induced by Aβ oligomers," Neurobiol. Aging, vol. 29, No. 9, 2008, pp. 1334-1347.
Deture et al., "tau Assembly in Inducible Transfectants Expressing Wild-Type of FTDP-17 tau," Americal Journal of Pathology, vol. 161, No. 5, pp. 1711-1722.
Galasko et al., "Assessment of CSF levels of tau protein in mildly demented patients with Alzheimer's disease," Neurology, vol. 48, 1997, pp. 632-635.
Gamblin et al., "Caspase cleavage of tau: Linking amyloid and neurofibrillary tangles in Alzheimer's disease," PNAS, vol. 100, No. 17, 2003, pp. 10032-10037.
Ghoshal et al., "Tau-66: evidence for a novel tau conformation in Alzheimer's disease," Jouranl of Neurochemistry, vol. 77, 2001, pp. 1372-1385.
Goedert et al., "Cloning and sequencing of the cDNA encoding an isoform of microtubule-associated protein tau containing four tandem repeats: differential expression of tau protein mRNAs in human brain, " The EMBO Journal, vol. 8, No. 2, 1989, pp. 393-399.
Goedert et al., "Multiple Isoforms of Human Microtubule-Associated Protein Tau: Sequences and Localization in Neurofibrillary Tangles of Alzheimer's Disease," Neuron, vol. 3, 1989, pp. 519-526.
Gomez-Ramos et al., "Extracellular tau promotes intracellular calcium increase through M1 and M3 muscarinic receptors in neuronal cells," Mol. Cell Neurosci., vol. 37, No. 4, 2008, pp. 673-681.
Guerrero et al., Abstract only for "Characterization and relevance of novel anti-oligomer mouse monoclonal antibody," presented to Society for Neuroscience, Nov. 2010.
Haines et al., "Germline diversity of the expressed BALB/c VhJ558 gene family," Molecular Immunology, vol. 38, 2001, pp. 9-18.
Hamano et al., "Concentration-dependent Effects of Proteasomal Inhibition on tau Processing in a Cellular Model of Tauopathy," Int. J. Clin. Exp. Pathol., vol. 2, 2009, pp. 561-573.
Hardy et al., "Amyloid deposition as the central event in the aetiology of Alzheimer's disease," Trends in Pharmacological Sciences, vol. 12, 1991, pp. 383-388.
Hardy et al., "The Amyloid Hypothesis of Alzheimer's Disease: Progress and Problems on the Road to Therapeutics," Science, vol. 297, 2002, pp. 353-356.
Haroutunian et al., "Tau protein abnormalities associated with the progression of alzheimer disease type dementia," Neurobiology of Aging, vol. 28, 2007, pp. 1-7.
Hernandez et al., "Tau Aggregates and Tau Pathology," Journal of Alzheimer's Disease, vol. 14, 2008, pp. 449-452.
Herukka et al., "CSF Aβ42 and tau or phosphorylated tau and prediction of progressive mild cognitive impairment," Neurology, vol. 64, 2005, pp. 1294-1297.
Holliger et al., "Engineered antibody fragments and the rise of single domains," Nature Biotechnology, vol. 23, No. 9, 2005, pp. 1126-1136.
Honson et al., "Tau aggregation and toxicity in tauopathic neurodegenerative diseases," J. Alzheimers Dis., vol. 14, No. 4, 2008, pp. 417-422.
Honson et al., "Small-Molecule Mediated Neuroprotection in an In Site Model of Tauopathy," Neurotox. Res., vol. 15, 2009, pp. 274-283.
Iqbal et al., "Mechanisms of tau-induced neurodegeneration," Acta Neuropathol., vol. 118, No. 1, 2009, pp. 53-69.

(56) References Cited

OTHER PUBLICATIONS

Jakes et al., "Identification of 3- and 4-repeat tau isoforms within the PHF in Alzheimer's disease," The EMBO Journal, vol. 10, No. 10, 1991, pp. 2725-2729.
Jones et al., "The Tenascin Family of ECM Glycoproteins: Structure, Functions, and Regulation During Embryonic Development and Tissue Remodeling," Developmental Dynamics, vol. 218, 2000, pp. 235-259.
Kayed et al., "Common Structure of Soluble Amyloid Oligomers Implies Common Mechanism of Pathogenesis," Science, vol. 300, 2003, pp. 486-489.
Kayed et al., "Permeabilization of Lipid Bilayers is a Common Conformation-dependent Activity of Soluble Amyloid Oligomers in Protein Misfolding Diseases," The Journal of Biological Chemistry, vol. 279, No. 45, 2004, pp. 46363-46366.
Kayed et al., "Conformation-Dependent Anti-Amyloid Oligomer Antibodies," Methods in Enzymology, vol. 413, 2006, pp. 326-344.
Kayed et al., "Prefilament tau species as potential targets for immunotherapy for Alzheimer disease and related disorders," Current Opinion in Immunology, vol. 21, 2009, pp. 359-363.
Kayed et al., Abstract only for "Oligomers role in amyloid formation via seeding and cross-seeding," presented to Society for Neuroscience, Oct. 2014.
Kurt et al., "Hyperphosphorylated tau and paired helical filament-like structures in the brains of mice carrying mutant amyloid precurser protein and mutant presenilin-1 transgenes," Neurobiology of Disease, vol. 14, 2003, pp. 89-97.
Lai et al., "Examination of Phosphorylated Tau Protein as a PHF-Precursor at Early Stage Alzheimer's Disease," Neurobiology of Aging, vol. 16, No. 3, 1995, pp. 433-445.
Lee et al., "Neurodegenerative Tauopathies," Annual Review of Neuroscience, vol. 24, 2001, pp. 1121-1159.
Li et al., "CSF tau/Aβ42 ratio for increased risk of mild cognitive impairment," Neurology, vol. 69, 2007, pp. 631-639.
Lindblad, "Aluminum compounds for use in vaccines," Immunology and Cell Biology, vol. 82, 2004, pp. 497-505.
Maeda et al., "Granular Tau Oligomers as Intermediates of Tau Filaments," Biochemistry, vol. 46, 2007, pp. 3856-3861.
Maguire-Zeiss et al., "Identification of human α-synuclein specific single chain antibodies," Biochemical and Biophysical Research Communications, vol. 349, 2006, pp. 1198-1205.
Margittai et al., "Template-assisted filament growth by parallel stacking of tau," PNAS, vol. 101, No. 28, 2004, pp. 10278-10283.
Margittai et al., "Side Chain-dependent Stacking Modulates Tau Filament Structure," The Journal of Biological Chemistry, vol. 281, No. 49, 2006, pp. 37820-37827.
Marx, "Alzheimer's Disease: A New Take of Tau," Science, vol. 316, 2007, pp. 1416-1417.
McKhann, "Metachromatic leukodystrophy: clinical and enxymatic parameters," Neuropediatrics, 1984, Suppl. 15, pp. 4-10.
Mena et al., "Monitoring pathological assembly of tau and β-amyloid proteins in Alzheimer's disease," Acta Neuropathol., vol. 89, 1995, pp. 50-56.
Mena et al., "Staging the pathological assembly of truncated tau protein into paired helical filaments in Alzheimer's disease," Acta Neuropathol., vol. 91, 1996, pp. 633-641.
Oddo et al., "Reduction of Soluble Aβ and Tau, but Not Soluble Aβ Alone, Ameliorates Cognitive Decline in Transgenic Mice with Plaques and Tangles," The Journal of Biological Chemistry, vol. 281, No. 51, pp. 39413-39423.
Parnetti et al., "Diagnosing prodromal Alzheimer's disease: Role of CSF biochemical markers," Mechanisms of Aging and Development, vol. 127, 2006, pp. 129-132.
Ringman et al., "Biochemical markers in persons with preclinical familial Alzheimer disease," Neurology, vol. 71, 2008, pp. 85-92.
Rosenmann et al., Tauopathy-like Abnormalities and Neurologic Deficits in Mice Immunized with Neuronal Tau Protein, Arch. Neurol., vol. 63, 2006, pp. 1459-1467.
Sahara et al., "Assembly of tau in transgenic animals expressing P301L tau: alternation of phosphorylation and solubility," Journal of Neurochemistry, vol. 83, 2002, pp. 1498-1508.
Sahara et al., "Tau Oligomerization: A Role for Tau Aggregation Intermediates Linked to Neurodegeneration," Current Alzheimer Research, vol. 5, 2008, pp. 591-598.
Santacruz et al., "Tau Suppression in a Neurodegenerative Mouse Model Improves Memory Function," Science, vol. 309, 2005, pp. 476-481.
Schneider et al., "Tau-Based Treatment Strategies in Neurodegenerative Diseases," Neurotherapeutics: The Journal of the American Society for Experimental NeuroTherapeutics, vol. 5, 2008, pp. 443-457.
Sengupta et al., Abstract only for "Tau oligomers in Parkinson disease and dementia with Lewy bodies and their connection with α-synuclein oligomers," presented to Society for Neuroscience, Nov. 2010.
Shaw et al., "Cerebrospinal Fluid Biomarker Signature in Alzheimer's Disease Neuroimaging Initiative Subjects," Ann. Neurol., vol. 65, No. 4, 2009, pp. 403-413.
Solit et al., "BRAF mutation predicts sensitivity to MEK inhibition," Nature, vol. 439, 2006, pp. 358-362.
Spires-Jones et al., "Tau pathophysiology in neurodegeneration: a tangled issue," Trends in Neurosciences, vol. 32, No. 3, 2009, pp. 150-159.
Tsitsopoulos et al., "Amyloid-β peptides and tau protein as biomarkers in cerebrospinal and interstitial fluid following traumatic brain injury: a review of experimental and clinical studies," Frontiers in Neurology, vol. 4, Article 79, 2013, pp. 1-17.
Vandermeeren et al., "Detection of tao Proteins in Normal and Alzheimer's Disease Cerebrospinal Fluid with a Sensitive Sandwich Enzyme-Linked Immunosorbent Assay," Journal of Neurochemistry, vol. 61, 1993, pp. 1828-1834.
Vieira et al., "Soluble oligomers from a non-disease related protein mimic Aβ-induced tau hyperphophorylation and neurodegeneration," Journal of Neurochemistry, vol. 103, 2007, pp. 736-748.
Vigo-Pelfrey et al., "Elevation of microtubule-associated protein tau in the cerebrospinal fluid of patients with Alzheimer's disease," Neurology, vol. 45, No. 4, 1995, pp. 788-793.
Walsh et al, "Aβ Oligomers—a decade of discovery," Journal of Neurochemistry, vol. 101, 2007, pp. 1172-1184.
Wiltfang et al., "Consensus Paper of the WFSBP Task Force on Biological Markers of Dementia: The role of CSF and blood analysis in the early and differential diagnosis of dementia," The World Journal of Biological Psychiatry, vol. 6, No. 2, 2005, pp. 69-84.
Wischik et al., "Structural characterization of the core of the paired helical filament of Alzheimer disease," Proc. Natl. Acad. Sci. USA, vol. 85, 1988, pp. 4884-4888.
Wischik et al., "Selective inhibition of Alzheimer disease-like tau aggregation by phenothiazines," Proc. Natl. Acad. Sci. USA, vol. 93, 1996, pp. 11213-11218.
Yagi et al., "Amyloid Fibril Formation of α-Synuclein is Accelerated by Preformed Amyloid Seeds of Other Proteins," The Journal of Biological Chemistry, vol. 280, No. 46, 2005, pp. 38609-38616.
Yoshiyama et al., "Synapse Loss and Microglial Activation Precede Tangles in a P301S Tauopathy Mouse Model," Neuron, vol. 53, 2007, pp. 337-351.
Zetterberg et al., "Cerebrospinal fluid markers for prediction of Alzheimer's disease," Neuroscience Letters, vol. 352, 2003, pp. 67-69.

* cited by examiner

Control; ICV, 1 µl of (1 mg/ml) control mouse mAb.
Treated; 1 µl of TOMA (1 mg/ml)

METHODS OF TREATING BRAIN INJURY

PRIORITY

This application is a continuation-in-part of U.S. application Ser. No. 13/393,220 having a 371(c) date of Oct. 1, 2012, which is a national stage application of PCT/US2010/047154 filed Aug. 30, 2010, which claims priority to U.S. Provisional Application Ser. No. 61/237,861 filed Aug. 28, 2009; and U.S. application Ser. No. 13/273,507 filed Oct. 14, 2011, which claims priority to U.S. Provisional Application Ser. No. 61/393,685 filed Oct. 15, 2010. This application also claims priority to U.S. Provisional Application Ser. No. 61/886,141 filed Oct. 3, 2013. Priority is claimed to all of the above referenced applicant, all of which are incorporated herein by reference in their entirety.

BACKGROUND OF THE INVENTION

I. Field of the Invention

Embodiments of this invention are directed generally to biology and medicine. In certain aspects, embodiments are directed to compositions and methods related to Tau oligomers and Tau oligomer specific antibodies.

II. Background

Pathological aggregation of the microtubule-associated protein Tau and accumulation of neurofibrillary tangles (NFT) or other inclusions containing Tau are defining histopathological features of Alzheimer's disease (AD) and many neurodegenerative diseases collectively known as tauopathies, including Pick's disease (PiD), progressive supranuclear palsy (PSP), corticobasal degeneration (CBD), and frontotemporal lobar degeneration (FTLD). The correlation between neurofibrillary tangles (NFT) and disease progression has been studied extensively with conflicting results, and the mechanisms linking the pathological aggregation of Tau with synaptic dysfunction and neurodegeneration are poorly understood.

In the case of Alzheimer's disease, current pharmaceutical therapies are focused on symptomatic treatment of the loss of cholinergic transmission, which results from neurodegeneration (Mayeux et al., 1999). However, although the available treatments delay progression of the disease for up to six to twelve months, they do not prevent it. The discovery of drugs that could prevent the aggregation of Tau, which leads to neurodegeneration, would provide a more effective strategy for prophylaxis or for inhibiting the progression of the disease, which would not require an immediate knowledge of the diverse upstream events that initiate the aggregation.

Furthermore, the clinical diagnosis of Alzheimer's disease (AD) is difficult to make, especially in early stages of the disease. Today, the diagnosis is based on a typical medical history combined with the exclusion of other causes of dementia. Certain clinical centers can have a diagnostic accuracy of 85-90% compared with the neuropathological diagnosis. In the early stages of the disease the clinical picture is vague and definite diagnostic markers have not yet been identified (McKhann, 1984). The development of biochemical diagnostic markers is important for a number of reasons: to support the clinical diagnosis, to allow clinicians to give adequate information to patients and their relatives, to initiate pharmacological treatment and care-giving, and in various aspects of clinical research.

Thus, in view of the prior art techniques for preventing and treating tauopathies, there is a need for a technique that enables earlier detection of markers of Alzheimer's disease.

SUMMARY OF THE INVENTION

Evidence indicates that intermediate sized aggregates of neurodegenerative disease associated proteins called oligomers (e.g., Tau oligomers) are the true pathogenic entities, rather than larger aggregates such as neurofibrillary tangles. Aspects described herein are directed to methods and reagents using or directed to Tau oligomers. In certain aspects, passive immunotherapy is use in treating tauopathies. In further aspects, administration of isolated Tau oligomers is use in treating tauopathies. In still other aspects Tau oligomer monoclonal antibodies (TOMAs) are used in treating or evaluating tauopathies. Compositions and methods described herein can be used to identify pathogenic or potentially pathogenic conditions—for example, the detection of Tau oligomers can be used as an early biomarker for tauopathies. In certain aspects the compositions can be used as a novel treatment for Tau related conditions. In certain aspects TOMA can be used to reduce NFTs, or reduce or inhibit the formation of NFTs. In other aspects, Tau oligomers can be used to induce antibodies that reduce NFTs or reduce the formation of NFTs.

Certain aspects of the invention are directed to an antibody that specifically binds Tau oligomers. In certain aspects, the antibody does not significantly bind soluble Tau or Tau fibrils. In a further aspect the antibody of the invention does not specifically bind soluble Tau or Tau fibrils. In certain embodiments the antibody is a monoclonal antibody or antibody fragment that specifically binds Tau oligomers and does not bind soluble Tau or Tau fibrils. The distinction between the soluble Tau, Tau oligomers, and Tau fibrils includes differences in conformation and stability. This is similar to amyloid oligomers and protofibrils that display different conformation with amyloid oligomers having a visible spherical like structure under the electron microscope and the atomic force microscope, the size of these structures is typically 2.5-20 nm. In contrast, fibrils under the microscope have a smooth appearance. The term "Tau oligomer" refers to a protein aggregate having about 3 to 24 Tau polypeptides or proteins or segments thereof. The term "soluble Tau" refers to a monomer or dimer of Tau proteins. The term "Tau fibrils" refers to insoluble Tau aggregate differing in conformation (e.g., having distinct epitopes as compared to Tau oligomer) and differing in phosphorylation status from Tau oligomers—Tau fibrils are more stable than Tau oligomers. In a further aspect, an antibody of the invention is a single chain antibody. The antibody can be a human antibody or a humanized antibody. In other aspects the antibody is comprised in a pharmaceutically acceptable excipient. Tau oligomer monoclonal antibodies (TOMA) can be used to analyze Tau oligomers in animal models and humans, as well as biological fluids from patients with or suspected of having tauopathies such as Alzheimer's disease (AD) and many neurodegenerative diseases, including Pick's disease (PiD), progressive supranuclear palsy (PSP), corticobasal degeneration (CBD), and frontotemporal lobar degeneration (FTLD) using TOMA in ELISA assay.

In certain aspects Tau oligomer specific antibodies can be used to evaluate subjects that have sustained or are suspected of having traumatic brain injury (TBI) or chronic traumatic encephalopathy (CTE). Tau oligomer specific antibodies can be used to identify subjects having TBI or CTE. In certain embodiments, the therapeutic compositions can be administered using various regimens, including variations in frequency and time period, sufficient to treat or provide a therapeutic benefit to the subject. In some embodiments, the subject is treated within at least 1 hr, within at least 2 hr, within at least 4 hr, within at least 6 hr, within at least 8 hr, within at least 10 hr, within at least 12 hr, within at least 14 hr, within at least 16 hr, within at least 18 hr, within at least 20 hr, within at least 22 hr, or within at least 24 hr of suffering the traumatic brain injury. In some embodiments, the subject is treated for at least 7 days, at least 14 days, or at least 28 days after suffering the traumatic brain injury.

Certain embodiments are directed to methods of protecting the brain of a subject after an activity or event associated with a potential traumatic brain injury by administering a therapeutic compositions described herein. The phrase "protecting the brain" refers to the reduction or elimination of the pathological effects associated with a concussion, in particular, minimizing the learning and/or memory deficits associated with traumatic brain injury, e.g., a concussion; improving a score on the Glasgow Coma Scale or other brain assessment regime, or an increase in brain resilience in the event of traumatic brain injury, e.g., reducing the time required after the traumatic brain injury to reduce/eliminate any learning and/or memory deficits. In certain aspects the activity or event associated with a traumatic brain injury is a vehicular impact, a fall, a sport (e.g., boxing, football, soccer, or hockey), a bullet wound, percussion from an explosion, or brain surgery.

In some embodiments, the invention is directed to a method of protecting the brain of a human subject or ameliorating brain injury, the method comprising: (1) identifying a subject who has experienced a traumatic brain injuring event, and (2) administering to the subject, after the traumatic brain injuring event, a therapeutic composition described herein.

Certain embodiments of the invention are directed to methods of preparing pathogenic Tau oligomers. These methods of preparing Tau oligomers mimic Tau aggregation in vivo. In this method Aβ oligomers and α-synuclein oligomers are used as promoters to cause Tau aggregation in vitro. Certain aspects are directed to methods of preparing Tau oligomers, comprising one or more steps of: (a) contacting an isolated recombinant Tau protein with a nucleation agent comprising preformed oligomers of an amyloid polypeptide, an α-synuclein polypeptide, or a prion polypeptide forming a nucleation mixture; (b) incubating the nucleation mixture under conditions that produce or promote Tau oligomerization; and/or (c) altering the conditions of the nucleation mixture such that Tau oligomerization stops or is reduced significantly. In certain aspects the amyloid polypeptide is Aβ42 or Aβ40. In a further aspect the prion polypeptide is prion 106-126. In certain embodiments preformed oligomer to Tau protein ratio is at least a 1:50, 1:100:1:120, 1:140, 1:160, 1:180, 1:200, or 1:500 (w/w) ratio, including all values and ranges there between. In further aspects the nucleation mixture is incubated for about or less than about 0.5, 0.75. 1. 1.25, 1.5, 1.75, 2, 2.5, or 3 hrs including all values and ranges there between. In certain aspects the nucleation mixture is incubated for at least 20, 30, 40, 50, 60, 70, 80, 90, 100, 120 minutes and at most 100, 120, 140, 180, 200, 220, 240, 260, 280, 300 minutes, including all values and ranges there between. In certain aspects the nucleation mixture is incubated for at least 50 minutes and at most 120 minutes. Other aspects of the invention are directed to a Tau oligomer produced by the methods described herein. Tau dimers are approximately 80 Kd to 1500 Kd, β-sheet rich, toxic to cells, sensitive to denaturating conditions, urea, guanidine formic acid and strong detergents.

Further aspects of the invention are directed to methods of identifying a Tau oligomer specific antibody comprising: (a) independently contacting antibodies that bind Tau oligomers with Tau oligomers, soluble Tau, or Tau fibrils; and (b) identifying antibodies that specifically bind Tau oligomers and do not bind soluble Tau or Tau fibrils at levels that are detectable above background. In certain aspects antibodies that specifically bind Tau oligomers and do not bind soluble Tau at levels detectable above background and do not bind Tau fibrils at levels detectable above background are identified by immunoblotting or ELISA assay.

In yet further aspects of the invention include methods of evaluating a patient suspected of or having a tauopathy comprising the step of detecting binding of an Tau oligomer specific antibody to a component of a biological sample from the patient, wherein the detection of Tau oligomer in the biological sample is indicative of tauopathy. In certain aspects the methods include evaluating a patient suspected of or having a traumatic brain injury (TBI) or chronic traumatic encephalopathy (CTE) comprising the step of detecting binding of a Tau oligomer specific antibody to a component of a biological sample from the patient, wherein the detection of Tau oligomer in the biological sample is indicative of TBI or CTE. The tauopathy can be Alzheimer's disease, Pick's disease (PiD), progressive supranuclear palsy (PSP), corticobasal degeneration (CBD), or frontotemporal lobar degeneration (FTLD). In certain aspects Tau oligomer is detected by immunoassay. A biological sample includes, but is not limited to blood, plasma, serum, platelets, cerebrospinal fluid (CSF), saliva, brain tissue, or neuronal tissue. In certain aspects the Tau oligomer specific antibody comprises a detectable agent. The detectable agent can include, but is not limited to a radioactive marker, a nucleic acid, a fluorescent label, or an enzymatic label.

In yet another aspect is directed to methods for treating a tauopathy comprising the step of administering an effective amount of a Tau oligomer or a Tau oligomer specific antibody to a subject having or suspected of having AD or other tauopathies. In certain aspects the methods include treating TBI or CTE comprising the step of administering an effective amount of a Tau oligomer or a Tau oligomer specific antibody to a subject having or suspected of having TBI or CTE. A Tau oligomer or an antibody specific for Tau oligomer can be administered at dose of about, at least, or at most 0.1, 0.5, 1, 2, 3, 4, 5, 6 µg or mg to 5, 6, 7, 8, 9, 10 µg or mg, including all values and ranges there between. The Tau oligomer or Tau oligomer specific antibody can be administered into the blood or CSF. Tauopathies that can be treated with these methods include, but are not limited to Pick's disease (PiD), progressive supranuclear palsy (PSP), corticobasal degeneration (CBD), and frontotemporal lobar degeneration (FTLD). In certain aspects, Tau oligomers are used to induce an immune response to treat a tauopathy (e.g., AD) or modify symptoms of tauopathies.

In other aspects, methods of treating a tauopathy or inducing an immune response to Tau oligomers comprises administering an effective amount of a Tau oligomer to a subject having or suspected of having a tauopathy, such as, but not limited to Pick's disease (PiD), progressive supranuclear palsy (PSP), corticobasal degeneration (CBD), and frontotemporal lobar degeneration (FTLD).

As used herein, the term "antigen" is a molecule capable of being bound by an antibody or T-cell receptor. An antigen is additionally capable of inducing a humoral immune response and/or cellular immune response leading to the production of B- and/or T-lymphocytes. The structural aspect of an antigen, e.g., three dimensional conformation or modification (e.g., phosphorylation), that give rise to a biological response is referred to herein as an "antigenic determinant" or "epitope." B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant need not be a contiguous sequence or segment of protein and may include various sequences that are not immediately adjacent to one another. In certain aspects, Tau oligomers are utilized as antigens.

The phrase that a molecule "specifically binds" or "specifically immunoreactive" to a target refers to a binding reaction that is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select antibodies specifically immunoreactive with a protein. See, e.g., Harlow and Lane (1988), for a description of immunoassay formats and conditions that can be used to determine specific immunoreactivity. Specific binding between two entities means an affinity of at least $10^6$, $10^7$, $10^8$, $10^9$ $M^{-1}$, or $10^{10}$ $M^{-1}$. Affinities greater than $10^8 M^{-1}$ are preferred.

The term "antibody" or "immunoglobulin" is used to include intact antibodies and binding fragments/segments thereof. Typically, fragments compete with the intact antibody from which they were derived for specific binding to an antigen. Fragments include separate heavy chains, light chains Fab, Fab' F(ab')2, Fabc, and Fv. Fragments/segments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann (1990); Kostelny et al. (1992).

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The terms "inhibiting," "reducing," or "prevention," or any variation of these terms, when used in the claims and/or the specification includes any measurable decrease or complete inhibition to achieve a desired result, e.g., a reduced pathogenic activity of Tau oligomers.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

As shown in FIG. 8B using T2286, this figure using TOMA confirms that tau oligomers are elevated in the CSF of AD patients vs. controls, measured by ELISA FIG. 10. TOMA single ICV injection reversed phenotypes in 7 months old P301L transgenic mice in four days: Before ICV injection; mice were tested twice one session a day using rotarod, in each session mice were placed four times over the rod. Initial speed of the rod was 4 r.p.m., after 30 seconds at 4 r.p.m., the speed was increasing at 0.1 r.p.m./second. Four days after the injection, mice were tested using same conditions used prior to injection. Control; were injected with 1 µl of 1 mg/ml control mouse monoclonal antibody (Rhodamine mmAb (Genetex cat#GTX29093). Treated; were injected with 1 µl of TOMA-1 (1 mg/ml). ** Statistically significant at $P<0.01$, 5 animals were used in each group.

DETAILED DESCRIPTION OF THE INVENTION

Figure 1:
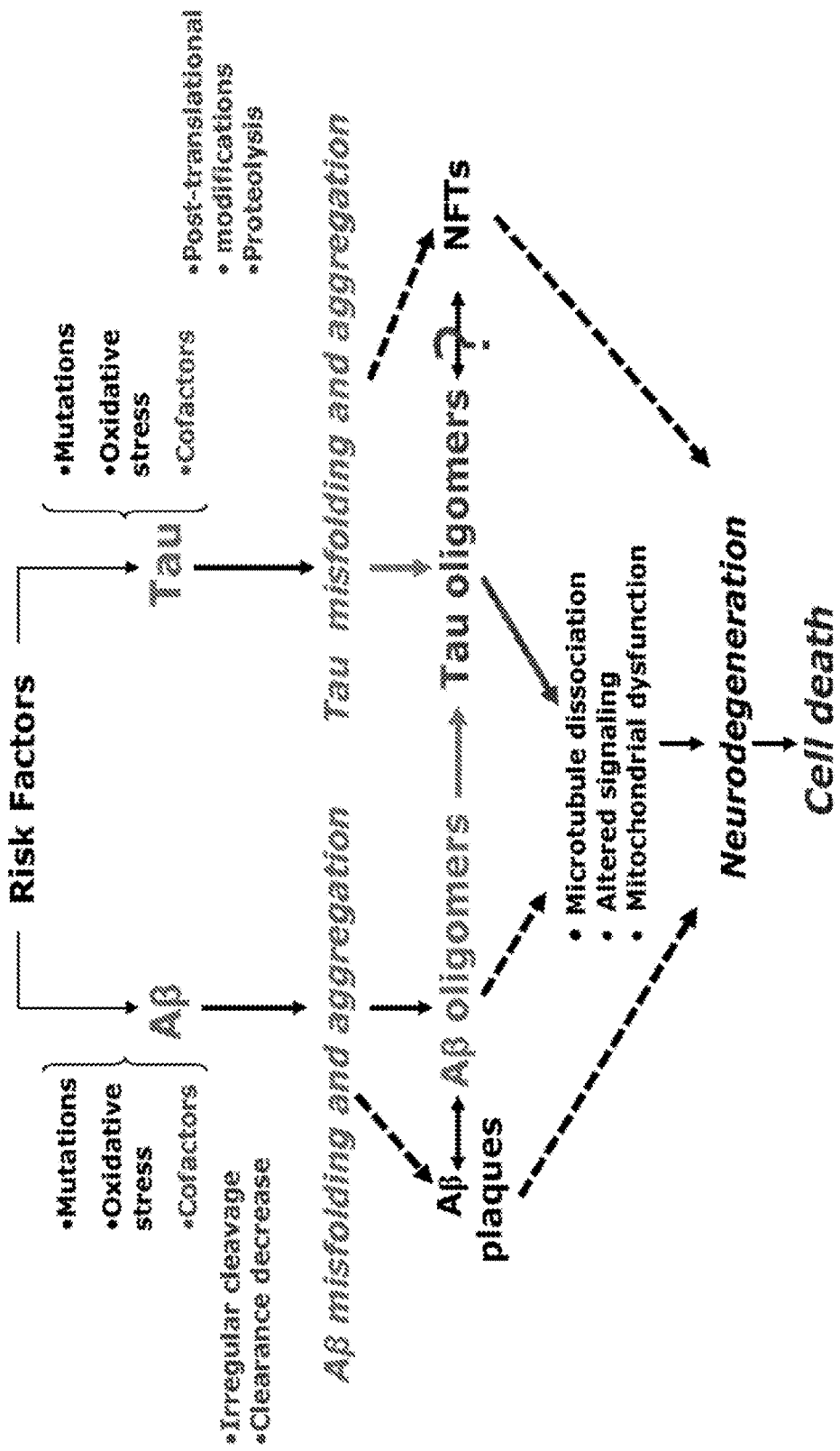
FIG. 1. A schematic illustrating the central role of tau oligomers in neurodegenerative diseases. AD and tauopathies are characterized by the deposition of tau or tau and another specific protein. Recently, studies from multiple laboratories have provided compelling evidence for the formation and pathogenic role of a tau species other than soluble monomeric tau or NFTs. This tau intermediate aggregate (tau oligomers) can cause neurodegeneration and memory impairment in the absence of Aβ; moreover, its formation may be critical for Aβ mediated neurotoxicity, thus identifying a target for immunotherapy and other approaches.
Figures 2A, 2B, 2C, 2D, 2E:
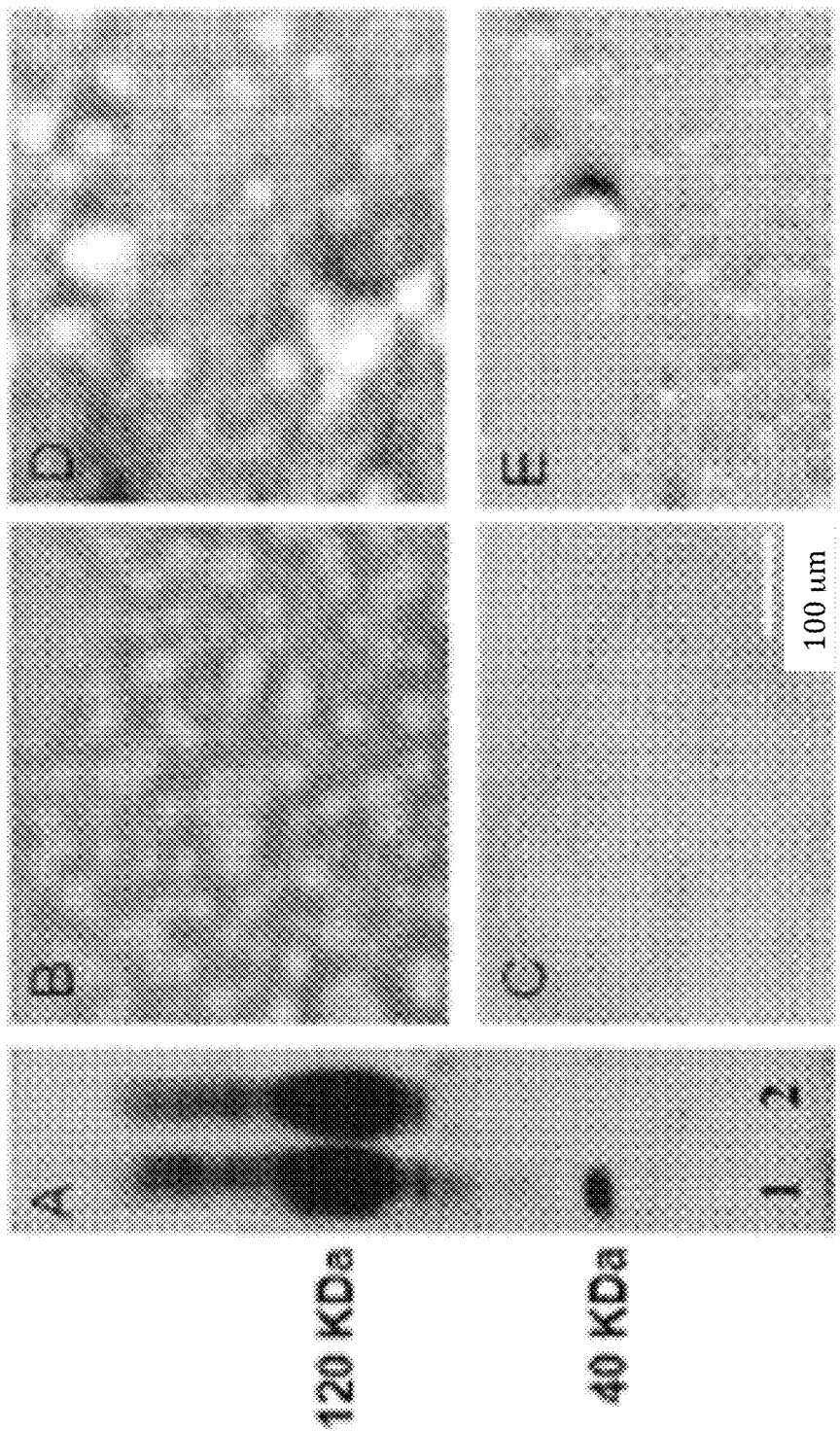
FIGS. 2A-2G. Tau oligomers prepared by seeding with preformed oligomers in PBS, pH 7.4 at a ratio of 1:140 (w/w) oligomers/tau. (A), Western blot of tau oligomers prepared by cross-seeding; 10 μM recombinant human tau (2N4R tau 1-441) seeded using α-synuclein oligomers (lane 1), Aβ42 oligomers (lane 2), probed with Tau5 antibody recognizing total tau. (B-C) EM images of tau oligomers prepared by seeding with Aβ42 oligomers. (D-E) AFM images of oligomers prepared by seeding with α-synuclein oligomers. (F) CD confirms that tau oligomers are β-sheet-rich, unlike unordered monomeric tau. (G) FPLC chromatogram of tau oligomers; the main peak is ~150-190 kDa, some larger tau oligomers eluted with the void peak.
Figures 2F, 2G:
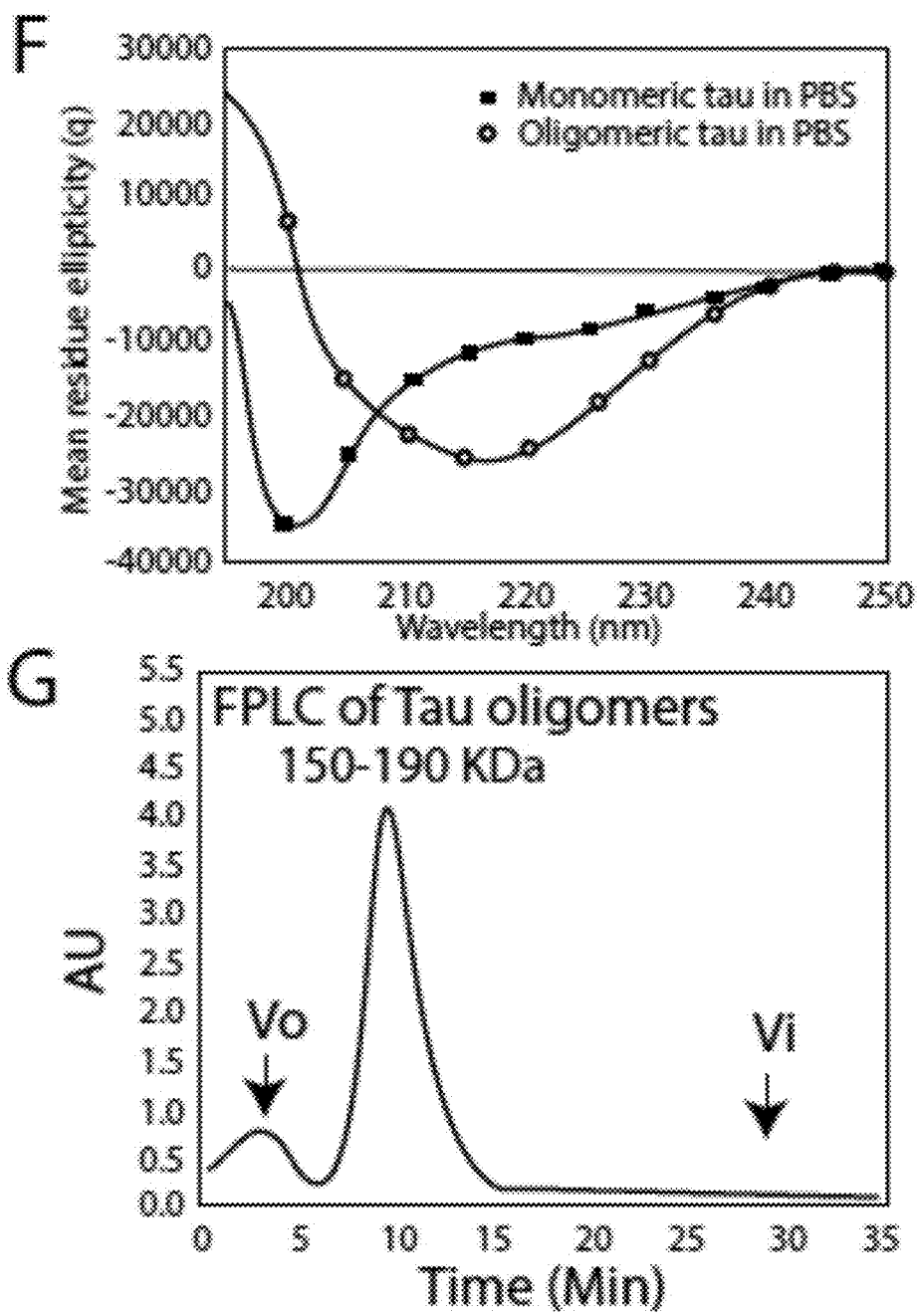

Pathological aggregation of the microtubule-associated protein Tau and accumulation of neurofibrillary tangles (NFT) or other inclusions containing Tau are defining histopathological features of many neurodegenerative diseases, including Alzheimer's disease (AD) which are collectively known as tauopathies. Tauopathies include, but are not limited to Pick's disease (PiD), progressive supranuclear palsy (PSP), corticobasal degeneration (CBD), and frontotemporal lobar degeneration (FTLD). As described herein Tau aggregates can also indicate traumatic brain injury (TBI) and chronic traumatic encephalopathy (CTE). The correlation between neurofibrillary tangles (NFT) and disease progression has been studied extensively with conflicting results, and the mechanisms linking the pathological aggregation of Tau with synaptic dysfunction and neurodegeneration are poorly understood. An emerging view is that NFT themselves are not the true toxic entity in tauopathies; rather, aggregates of a size intermediate between monomers and NFT—so-called Tau oligomers—are pathogenic. Investigating such oligomers requires new methods and tools. Methods are described herein for the preparation and use of homogenous populations of Tau oligomers. These Tau oligomers are utilized in the production and characterization of monoclonal antibodies that specifically recognize Tau oligomers, Tau Oligomer Monoclonal Antibody (TOMA). Studies on post mortem brain and CSF indicates a surprising and novel role for Tau oligomers in tauopathies. Embodiments of the invention include compositions and methods for producing and using TOMAs of the invention in the evaluation and/or treatment of tauopathies. Other embodiments include compositions and methods for producing and using TOMAs of the invention in the evaluation and/or treatment of TBI and/or CTE.

I. TAU OLIGOMERS AND DISEASE

The Tau protein exists in alternatively-spliced isoforms, which contain three or four copies of a repeat sequence corresponding to the microtubule-binding domain (Goedert et al., 1989; Goedert et al., 1989). Tau is proteolytically processed to a core domain when it is in the form of paired helical filaments (PHFs) (Wischik et al., 1988a; Wischik et al., 1988b); Novak et al., 1993); only three repeats are involved in the stable tau-Tau interaction Oakes et al., 1991). Once formed, PHF-like Tau aggregates act as seeds for the further capture and provide a template for proteolytic processing of full-length Tau protein (Wischik et al., 1996).

In the course of their formation and accumulation, PHFs first assemble to form amorphous aggregates within the cytoplasm, probably from early Tau oligomers which become truncated prior to, or in the course of, PHF assembly (Mena et al., 1995; Mena et al., 1996). These filaments then go on to form classical intracellular neurofibrillary tangles. In this state, the PHFs consist of a core of truncated Tau and a fuzzy outer coat containing full-length Tau (Wischik et al., 1996). The assembly process is exponential, consuming the cellular pool of Tau and inducing new Tau synthesis to make up the deficit (Lai et al., 1995). Eventually, functional impairment of the neuron progresses to the point of cell death, leaving behind an extracellular tangle. Cell death is highly correlated with the number of extracellular tangles (Wischik et al., 2000). As tangles are extruded into the extracellular space, there is progressive loss of the fuzzy outer coat of the neuron-PHF with corresponding loss of N-terminal Tau immunoreactivity—with immunoreactivity associated with the PHF core preserved (Bondareff et al., 1994).

The phase shift which is observed in the repeat domain of Tau incorporated into PHFs suggests that the repeat domain undergoes an induced conformational change during incorporation into the filament. During the onset of Alzheimer's disease, it is envisaged that this conformational change could be initiated by the binding of Tau to a pathological substrate, such as damaged or mutated membrane proteins (see Wischik et al., 1997).

A. Tau Function, Phosphorylation and Neurofibrillary Tangles (NFT) Formation.

The microtubule-associated protein Tau is required for microtubule assembly, axonal transport and neurite outgrowth. Tau serves a crucial function in the cytoskeleton by organizing and stabilizing microtubules. Tau enhances the polymerization of tubulin dimers and stability of microtubules by enhancing the binding of GTP to β-tubulin (Binder et al., 1985). Most of the biological functions of Tau are modulated by site-specific phosphorylation (Drechsel et al., 1992). Tau is encoded by a single gene, but six splice isoforms ranging in size from 352 to 441 amino acids are expressed in the human CNS (SEQ ID NO:1-6) (Goedert et al., 1989). These isoforms differ from each other by the presence of 0, 1, or 2 N-terminal inserts, and 3 or 4 tandemly arranged microtubule-binding repeats; therefore, these isoforms are refer to as ON3R (SEQ ID NO:1), 1N3R (SEQ ID NO:2), 2N3R (SEQ ID NO:3), 0N4R (SEQ ID NO:4), 1N4R (SEQ ID NO:5) and 2N4R (SEQ ID NO:6). Aspects of the invention regard antibodies that bind Tau oligomers comprising one or more of these isoforms or segments thereof, or detection of Tau oligomers comprising one of more of these isoforms or segments thereof.

Tau undergoes many posttranslational modifications including, glycosylation, ubiquitination, glycation, polyamination, nitrosylation, and truncation. A disease relevant Tau posttranslational modification is hyperphosphorylation. Hyperphosphorylation can alter tau's biological functions and causes Tau self-assembly, aggregation, and accumulation in neurofibrillary tangles (NFT), a hallmark of AD and other neurodegenerative diseases (Alonso et al., 2008; Lee et al., 2001). All Tau isoforms contain at least 30 phosphorylation sites (Buee et al., 2000; Goedert et al., 1992), most of which are believed to be in the de-phospho form in normal tau. Some degree of phosphorylation at many of these sites occurs in normal Tau proteins; nevertheless, many of these sites are abnormally phosphorylated with respect to both location and quantity in NFT (Matsuo et al., 1994; Lee et al., 2001; Morishima-Kawashima et al., 1995). Tau phosphorylation, particularly at specific sites, such as serine 262 (S262), reduces its affinity for microtubules (Biernat et al., 1993), so it is not surprising that considerable attention has been paid to determining which protein kinases and phosphatases control Tau phosphorylation (Avila, 2008). Numerous Tau kinases have been found, including, but not restricted to MAPK (Drewes et al., 1992), GSK3β (Hanger et al., 1992), MARK (Drewes et al., 1995), cdk2 and cdk5 (Baumann et al., 1993). In contrast, PP2A appears to be the principal Tau phosphatase in vivo (Goedert et al., 1995); PP1, PP2B and PP2C are also capable of dephosphorylating Tau in vitro (Buee et al., 2000; Johnson et al., 2004).

A key early finding about Tau in NFT accumulated in AD and non-AD tauopathies was the fact that it is abnormally phosphorylated (Spires-Jones et al., 2009; Grundke-Iqbal et al., 1986). The sequence of early Tau phosphorylation suggests that there are events prior to NFT formation that are specific to particular phosphorylated Tau epitopes, leading to conformational changes and cytopathological alterations. Using phosphorylation dependent Tau antibodies, three stages of NFT development were introduced: (1) pre-NFT, (2) intra-neuronal, and (3) extra-neuronal NFT. The pre-NFT state, in which neurons display nonfibrillar, punctate regions in the cytoplasm, dendrites, somata, and nuclei, was observed especially with phospho-Tau antibodies TG3 (pT231), pS262, and pT153. Intraneuronal NFT were homogenously stained with fibrillar Tau structures, which were most prominently stained with pT175/181, 12E8 (pS262/pS356), pS422, pS46, and pS214 antibodies. Extracellular NFT, which contain substantial filamentous tau, are most prominently stained with AT8 (pS199/pS202/pT205), AT100 (pT212/pS214), and PHF-1 (pS396/pS404) antibodies, which also stain intracellular NFT. Moreover, the severity of AD and neuronal loss correlates with the patterns of Tau phosphorylation in NFT (Augustinack et al., 2002; Trinczek et al., 1995).

Tau hyperphosphorylation is thought to be an early event in the cascade leading from soluble to insoluble Tau protein, but evidence demonstrating that hyperphosphorylation is sufficient for filament formation is lacking Why does hyperphosphorylation promote aggregation of Tau proteins into abnormal filaments? Not to be limited to any particular theory, one possibility is that the negative charge imparted by phosphorylation neutralizes the basic charges of tau, thus facilitating intermolecular interaction and aggregation (Alonso et al., 2001a; Alonso et al., 2001b). An alternative explanation is that hyperphosphorylation detaches Tau from microtubules, thus increasing the pool of unbound tau. Unbound, hyperphosphorylated Tau may compete with microtubules for binding to normal Tau and other microtubule associated proteins, thereby sequestering them and enhancing disassembly of microtubules (Alonso et al., 2001a). As compared to microtubule-bound tau, this unbound Tau may be more degradation-resistant and more likely to aggregate. Reduced proteolysis of hyperphosphorylated Tau may also increase the pool of soluble Tau available for formation of paired helical filaments (PHF). Thus, abnormal phosphorylation of Tau may result in an increase in the total cellular pool of tau, and may change its solubility, thus negatively regulating stability of microtubules (Litersky et al., 1992; Litersky et al., 1993).

One important contributor to Tau phosphorylation and NFT formation may be amyloid. The "amyloid cascade" hypothesis holds that the accumulation of Aβ peptides in senile plaques results in the formation of NFT and neuronal cell death (Busciglio et al., 1995). In primary neuronal cultures, Aβ is capable of inducing Tau phosphorylation (Busciglio et al., 1995). Aβ42 fibrils induced formation of neurofibrillary tangles in P301L Tau transgenic mice (Gotz et al., 2001), and pre-aggregated Aβ42 induced PHF formation mediated by distinct phospho-epitopes of Tau in cells overexpressing wild-type and mutant forms of human Tau (Ferrari et al., 2003; Pennanen and Gotz, 2005). Aβ oligomers, but not the soluble or fibrillar forms of Aβ, induced Tau hyperphosphorylation in cells overexpressing human Tau (De Felice et al., 2008); this phenomenon is not Aβ-specific, but rather conformation specific, as demonstrated by the ability of soluble oligomers from a non-disease related protein, hen egg white lysozyme, to mimic Tau hyperphosphorylation induced by Aβ aggregates (Vieira et al., 2007).

The assembly of Tau aberrant filaments can be reproduced in vitro by using a high concentration of Tau protein or, at lower protein concentrations, by adding compounds including polyanions, fatty acids (and derivates), and others. The methods and conditions reported for in vitro Tau polymerization have been the subject of comprehensive reviews (Avila et al., 2004; Avila, 2000). Mechanistic studies of full length Tau protein aggregation and filament formation in vitro revealed striking similarities to the in vitro aggregation of Aβ via a nucleation-dependent mechanism (Honson et al., 2009).

B. Tau Deposition and its Causal Role in AD and Tauopathies.

Neuropathological features of tauopathies include filamentous neuronal or neuronal and glial Tau inclusions found in association with focal neurodegeneration. The aggregation of proteins including Tau and their deposition in many aggregated forms in AD and related neurodegenerative diseases have been studied extensively. Despite a strong body of evidence supporting an important role of Tau in AD (Ballatore et al., 2007; Haroutunian et al., 2007; Iqbal et al., 2009), the amyloid hypothesis (Hardy and Allsop, 1991; Hardy and Selkoe, 2002) proposes that Aβ is the sole cause of AD and that Tau aggregation is one of many downstream events triggered by Aβ aggregation and deposition. Tau is the main component in neuropil threads and NFT observed in AD; these extremely stable structures accumulate to high density in both axonal and somatodendritic compartments of AD neurons, in addition to extracellular β-amyloid deposits.

The size, appearance, and distribution pattern of amyloid deposits vary considerably between individual AD brains and correlate poorly with the disease severity. Neurofibrillary pathology, on the other hand, tends to develop at specific sites and follows a characteristic pattern with regard to region and cell types affected. NFT in AD patients are highly correlated with disease progression and can be used to stage AD by post mortem brain histopathology; moreover, Tau pathology appears to be essential for AD, because amyloid pathology in the absence of NFT is not necessarily associated with loss of cognitive function or appreciable neurodegeneration (Braak and Braak, 1991a; Alafuzoff et al., 2008; Braak and Braak, 1991b; Braak and Braak, 1996).

Mutations in the Tau gene, MAPT, cause familial frontotemporal dementia with parkinsonism linked to chromosome 17 (FTDP-17, now known as frontotemporal lobar degeneration-Tau (FTLD-Tau)), directly implicating Tau dysfunction in neurodegenerative processes (Clark et al., 1998; Hutton et al., 1998; Pittman et al., 2006). Interestingly, amyloid plaques are not found in individuals with FTLD-Tau. This discovery showed that abnormal forms of Tau are sufficient for neurodegeneration, causing memory loss and other neurological deficits.

Aged mice expressing non-mutant human Tau in the absence of mouse Tau (h-Tau mice) developed NFT and extensive cell death (Andorfer et al., 2005). Mice that conditionally express a mutant human Tau gene showed accumulation of NFT in neurons; the expression of Tau caused learning deficits and neurodegeneration. However, suppressing expression of the mutant Tau gene improved memory and halted neuronal loss (Santacruz et al., 2005). Hippocampal neurons from Tau knockout mice are resistant to β-amyloid-induced cell death, implicating Tau function in Aβ-related neurodegeneration in AD (Rapoport et al., 2002). Reducing endogenous Tau ameliorates Aβ-induced deficits in an AD mouse model; the mice with normal Tau levels showed age-related memory loss, behavioral abnormalities, and deposition of amyloid plaque. The mice with reduced levels of Tau showed a typical pattern of amyloid plaque accumulation but did not have memory loss or behavioral abnormalities (Ashe, 2007; Roberson et al., 2007). Reducing Aβ burden alone by immunotherapy is inadequate to reverse cognitive deficits in mice (3×Tg-AD) that contain both hallmarks of AD, plaques and NFT (Oddo et al., 2006). Taken together, these observations suggest that Tau aggregation is a critical mediator of neurodegeneration and has a causal role in AD and other tauopathies.

C. Tau in Traumatic Brain Injury and Chronic Traumatic Encephalopathy

Certain embodiments are directed to methods of treating traumatic brain injury (TBI). Traumatic brain injuries contribute to a substantial number of deaths and cases of permanent disability. Causes include, among others, falls, vehicle accidents, and violence. A traumatic brain injury is caused by a bump, blow or jolt to the head or a penetrating head injury that disrupts the normal function of the brain. Not all blows or jolts to the head result in traumatic brain injury. In certain aspects methods are provided for identifying a subject having a TBI. TBI can cause a host of physical, cognitive, emotional, and behavioral effects, and outcome can range from complete recovery to permanent disability or death. Neurobehavioral deficits, especially impaired cognitive function, are often the cause of significant disability after traumatic brain injury.

Traumatic brain injury (TBI) is a head injury caused by trauma to the brain. The damage can be confined to one area of the brain (focal) or involve more than one area of the brain (diffuse). TBI can be mild, moderate or severe. While some symptoms appear immediately, others do not appear until days, weeks, months or even years after the TBI event(s). Symptoms of mild TBI include headache, confusion, dizziness, blurred vision, changes in mood, and impairment in cognitive function, such as memory, learning, and attention. Symptoms of moderate to severe TBI include, in addition to those observed for mild TBI, nausea, convulsions or seizures, slurring of speech, numbness of extremities, and loss of coordination.

TBI often occurs as an acute event resulting from a motor vehicle accident, blast injury, fall, or gunshot wound to the head. Demonstration of neuronal and glial changes months after TBI, in combination with evidence of seizures, endocrine disorders, and circadian rhythm disruption, have led to an understanding that TBI is a chronic disease (as reviewed in Tsitsopoulos and Marklund, 2013). Repetitive neurotrauma is believed to contribute to the development of chronic traumatic encephalopathy (CTE) and can result in a progressive form of dementia reminiscent of early onset AD. Tau can be hyperphosphorylated (P-tau) and aggregate in TBI and CTE. The formation of NFTs has been observed after repetitive mild human TBI and after many years following a single severe TBI. In CTE, the vast majority of cases display widespread NFTs and A□ pathology is much less frequently observed.

Standard treatments for traumatic brain injury include administration of diuretics, anti-convulsants, and AMPA/NMDA receptor antagonists. However, it is desirable to have treatments that can provide subsequent trophic support to remaining central nervous system tissue, and thus enhance functional repair and recovery, under the complex physiological cascade of events that follow the initial insult in traumatic brain injury.

The presence of traumatic brain injury can be assessed by standard techniques used by a physician of skill in the art. These include, (a) Glasgow Coma Scale, which is a 15-point test to assess the severity of a brain injury by checking a subject's ability to follow directions, to blink the eyes or to move extremities; and (b) brain imaging techniques, including computer assisted tomography (CAT) scans, which allow visualization of fractures and evidence of bleeding in the brain (hemorrhage), large blood clots (hematomas), bruised brain tissue (contusions), and brain tissue swelling. In certain aspects, the brain imaging technique used is magnetic resonance imaging (MRI), including Susceptibility weighted images (SWI), a sensitive method for detecting small hemorrhages in the brain, and Diffusion tensor imaging (DTI), which consists of a minimum of six scans with diffusion gradients placed in an orthogonal manner. In some embodiments, traumatic brain injury can be assessed by measuring intracranial pressure, which can occur by swelling of the brain.

Since neurobehavioral, particularly cognitive related, problems are a major effect of traumatic brain injury, various methods used to assess cognitive function can be used. Such assessments include, among others, the following: Clinical Dementia Rating Scale (CDR), a dementia staging instrument that classifies cognitive impairment along a continuum from normal aging to mild cognitive impairment to all stages of dementia severity; Folstein Mini-Mental State Exam (MMSE), which is commonly used measure of orientation and gross cognitive functioning used by physicians and healthcare providers to screen for cognitive decline; and Alzheimer's Disease Assessment Scale-Cognitive (ADAS-C), a test commonly used in detection of dementia and mild cognitive impairment.

II. IN VITRO PRODUCTION OF TAU OLIGOMERS

Tau is a highly soluble and natively unfolded protein dominated by a random coil structure in solution. It is believed that aberrant modifications of tau, including phosphorylation, truncation, and conformational changes induce filamentous aggregation. The importance of pre-filament Tau aggregation intermediates (Tau oligomer) in disease pathogenesis was suggested by recent reports (Congdon and Duff, 2008; Brunden et al., 2008). However, the mechanism underlying the conversion of soluble Tau to soluble and insoluble aggregates remains elusive. The assembly of Tau into filaments could be reproduced in vitro by adding some compounds like polyanions, fatty acids (and derivates), and other known promoters (Kurt et al., 2003). Still, no reliable methods to prepare homogenous population of Tau oligomers are available, hindering the ability to evaluate Tau oligomer toxicity and its possible role in the disease.

It is know that amyloid fibrils can accelerate the aggregation of the same protein via nucleation-dependent mechanism (seeding). Recently, the inventor observed that amyloid oligomers such as fibrils could seed oligomer formation from the same protein. Moreover, the inventor discovered a surprising phenomena associated with amyloid oligomers—cross-seeding. In cross-seeding preformed oligomers from one protein can cause the aggregation and the formation of oligomers from other proteins having no sequence homology to the preformed oligomers (Kayed and Glabe, The SFN 36th annual meeting 2006, poster#17.6). Moreover, the inventor discovered that preformed oligomers from amyloid protein (e.g., Aβ42, A(340), α-synuclein, or prions (e.g., prion 106-126) can promote Tau oligomerization. It is known that aggregated forms of Aβ are capable of inducing Tau phosphorylation and aggregation both in primary neuronal cultures and Tau animal models (Busciglio et al., 1995; Gotz et al., 2001; Ferrari et al., 2003; Pennanen and Gotz, 2005; De Felice et al., 2008). A recent report demonstrated that this phenomena is not Aβ specific, but rather conformation specific, since soluble oligomers from a nondisease related protein, hen egg white lysozyme, were able to induce Tau hyperphosphorylation and aggregation in neuronal cultures similar to aggregated Aβ (Vieira et al., 2007). Studies on the kinetics of Tau aggregation when seeded with preformed oligomers led to the optimization of a reliable protocol for the preparation of homogeneous populations of Tau oligomers in vitro, an example of which is described below. Compositions were analyzed by immunoblotting and FPLC. After 1 hr of seeding isolated Tau oligomers had less than about 0.5, 0.75, 1, 1.5, to 2% soluble Tau and less that about 5, 10, to 15% Tau fibrils and at least, at most or about 80, 85, 90% to 90, 95% Tau oligomers.

An example of preparing Tau oligomers by cross-seeding includes expressing and purifying recombinant Tau protein (e.g., tau-441 (2N4R) M.W. 45.9 kDa) (Margittai and Langen, 2004; Margittai and Langen, 2006). Amyloid oligomers from Aβ42 or α-synuclein are prepared (Kayed and Glabe, 2006; Kayed et al., 2004). In one example, preformed Aβ42 oligomers were added to 10 μM soluble Tau in PBS pH 7.4 or in 10 mM HEPES pH 7.4 at a ratio of 1:140 (w/w) Aβ42 oligomers/tau. Control Tau samples are also incubated under the same conditions with Aβ42 fibrils, soluble Aβ42, and without any Aβ. Also, Aβ42 oligomers diluted 1:140 in both PBS and 10 mM HEPES were used to determine the background signal. The formation of soluble Tau oligomers after 1 hr was quantified by ELISA, and the signal of Aβ42 oligomers diluted in PBS or HEPES was subtracted. If samples show signs of precipitation they can b e centrifuged and the pellet is then washed 3 times with ddH$_2$O and resuspended in ddH$_2$O. The sample can be resuspended sample and applied to electron microscopy (EM) grid or mica for atomic force microscopy (AFM). Portions of the sample can also be applied to nitrocellulose membrane for blotting. Tau oligomers form at 50 min-180 min. After 2-3 hrs Tau protofibrils and fibrils start to form. The reaction can be stopped, for example, by raising the pH to 9.5-10.5. Freezing at −80° C. can also be employed in stopping the reaction—after thawing, oligomers with higher molecular weight can be broken down to smaller oligomers by using water sonication, e.g., sonication 2 times at 30 sec. These samples are stable at room temperature for more than a week. To produce Tau fibrils the cross-seeding was allowed to continue for 2 days. After 2 days fibrils were spun down by centrifugation. The Tau fibrils can then be washed with ddH20 (resuspension and centrifugation) and the pellet resuspended in PBS.

Electron microscopic and Atomic Force Microscopic images confirm that Tau oligomers have spherical morphology, similar to oligomers formed by other amyloidogenic proteins (Kayed et al., 2003; Kayed et al., 2004). Tau oligomers are capable of seeding soluble tau, β-sheet rich measured by circular dichroism (CD) spectroscopy, and toxic to cells measured by both MTS and Almar blue assays. On western blotting they form a ladder with a major band of 110-120 KDa (likely a trimer). After aging for two days at room temperature (in PBS pH 7.4), Tau oligomers convert into a very stable Tau fibrils; this transition is also evident by a disappearance of the trimeric band on western blot, and dramatic reduction in the toxicity. As expected, Tau oligomers prepared by this method are unphosphorylated—they did not react with the phospho-Tau antibody AT8.

III. TAU SPECIFIC ANTIBODIES

The term "antibody", as used herein, broadly refers to any immunoglobulin (Ig) molecule or Tau oligomer binding peptide derived from an antibody including any functional fragment, mutant, variant, or derivation thereof, which retains the essential epitope binding or Tau oligomer binding features of an Ig molecule that specifically binds Tau oligomer. Such mutant, variant, or derivative antibody formats are known in the art. In certain aspects and antibody is a monoclonal antibody or a single chain antibody. In still further aspects the antibody is a recombinant antibody segment that retains Tau oligomer specific binding.

Typically, antibodies are comprised of four polypeptide chains, two heavy (H) chains and two light (L) chains. In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyterminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG1, IgG2, IgG3, IgG4, IgA1 and IgA2) or subclass.

An "isolated antibody", as used herein, is intended to refer to an antibody that is substantially free of other antibodies having different antigenic specificities (e.g., an isolated antibody that specifically binds Tau oligomer is substantially free of antibodies that specifically bind antigens other than Tau oligomer). An isolated antibody that specifically binds Tau oligomer may, however, have cross-reactivity to other antigens, such as Tau oligomer from other species. Moreover, an isolated antibody may be substantially free of other cellular material and/or chemicals and/or any other Tau oligomer form that comprises the epitope with which the antibodies of the present invention are reactive.

The term "human antibody", as used herein, is intended to include antibodies having variable and constant regions derived from human immunoglobulin sequences. The human antibodies of the invention may include amino acid residues from human CDRs and in particular CDR3. However, the term "human antibody", as used herein, is not intended to include antibodies in which CDR sequences from another mammalian species, such as a mouse, have been grafted onto human framework sequences.

The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences.

As used herein, the term "humanized antibody" is an antibody or a variant, derivative, analog or segment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, more preferably at least 90%, more preferably at least 95%, more preferably at least 98% and most preferably at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain.

The antibody can be selected from any class of immunoglobulins, including IgM, IgG, IgD, IgA and IgE, and any isotype, including without limitation IgG1, IgG2, IgG3 and IgG4. The antibody may comprise sequences from more than one class or isotype, and particular constant domains may be selected to optimize desired effector functions using techniques well-known in the art.

The framework and CDR regions of an antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences.

Embodiments are directed to a monoclonal antibody or an antibody fragment that specifically binds an oligomer comprising all or part of a peptide having the amino acid sequence GKHGAGAAAAGAVVGGLGGYGLGSAGSR-PIIHFGSDYEDRY (SEQ ID NO:1), including peptides that are 80, 85, 90, 95, 98, 99, or 100% identical to SEQ ID NO:1. In certain aspects the monoclonal antibody or antibody fragment that binds an oligomer comprising a peptide of SEQ ID NO:1 is a mouse monoclonal antibody or mouse antibody fragment. In a further aspect the antibody can be a single chain antibody. In certain aspects the monoclonal antibody or antibody fragment is a humanized monoclonal antibody or antibody fragment. In certain aspects the monoclonal antibody is monoclonal antibody F11G3 or F8H7 or fragments thereof. The F11G3 heavy chain variable region has an amino acid sequence of EVQLQQSGPELVKPGAS-VKMSCKASGYTFTDYYMKWVKQSHGK-SLEWIGDINPNNGD TFYNQKFKGKATLT-VDKSSSTAYMQLNSLTSEDSAVYYCARGVYDGYY-AMDYWGQG TSVTVSS (SEQ ID NO:11). The F11G3 light chain variable region has an amino acid sequence of DIVMTQAAPSVPVTPGESVSISCRSSKSLLHSNGNTY-LYWFLQRPGQS PQLLIYRMSNLASGVPDRFSGSGSG-TAFTLRISRVEAEDVGVYYCMQHLEYPLTFGAGT KLELK (SEQ ID NO:12). The monoclonal antibody or antibody fragment can comprise an amino acid sequence that is 80, 85, 90, 95, 98, or 100% identical to the amino acid sequence of SEQ ID NO:11 and/or SEQ ID NO:12. In a further aspect a monoclonal antibody or fragment thereof is comprised in a composition, such as a diagnostic or pharmaceutically acceptable composition or formulation.

In certain aspects the compositions can be used as a novel treatment for amyloid related conditions including TBI. In certain aspects antibodies of the invention can be used to reduce amyloid aggregates, or reduce or inhibit the formation of amyloid aggregates. In other aspects, a peptide or an oligomer having the amino acid sequence of SEQ ID NO:1 can be used to induce antibodies that reduce amyloid aggregates, or reduce or inhibit the formation of amyloid aggregates.

In yet another aspect, to the invention provides methods for treating an amyloid related disease comprising the step of administering an effective amount of a peptide comprising or consisting of the amino acid sequence of SEQ ID NO:1 or an amyloid oligomer specific antibody that specifically binds a peptide having or consisting of the amino acid sequence of SEQ ID NO:1 to a subject having or suspected of having TBI or CTE. Such a peptide or an antibody specific for the peptide can be administered at a dose of about, at least, or at most 0.1, 10, 20, 50, 100, 200 mg/kg to 20, 50, 100, 200, 500 mg/kg, including all values and ranges there between. The peptide or antibody can be administered into the blood or CSF.

In other aspects, methods of treating an amyloid related disease or inducing an immune response to an immunogen comprising an amino acid sequence of SEQ ID NO:1 comprises administering an effective amount of a peptide or antigen composition to a subject having or suspected of having an amyloid related disease. In other aspects, passive immunotherapy can be used in treating amyloid diseases or conditions.

IV. DIAGNOSTIC USE OF TAU

In most cases of Alzheimer's disease (AD), the neurodegenerative process has progressed to an advanced stage with massive cell loss before a diagnosis can be made (Teunissen et al., 2002). The current methods of diagnosing clinical AD rely, in part, upon cognitive tests such as the MMSE (Folstein et al., 1975). Unfortunately, the MMSE has been reported to be insensitive to detecting preclinical or very early AD (Petersen et al., 1999). One of the criteria for an ideal marker for diagnosis is that it be able to detect a fundamental feature of AD neuropathology; the most obvious targets for analysis would therefore be Aβ and tau. Several groups have examined levels of these proteins (Borroni et al., 2006; Wiltfang et al., 2005), and others, in blood and urine without success (Borroni et al., 2006; Wiltfang et al., 2005). Tau levels are reported to be elevated in the CSF of AD and MCI patients as compared to normal controls (Andreasen et al., 1999; Galasko et al., 1997; Vandermeeren et al., 1993; Vigo-Pelfrey et al., 1995). In contrast, decreased Aβ42 CSF levels have been described (Andreasen et al., 1999; Motter et al., 1995). Further, these studies also determined that total Aβ levels were not significantly different among the diagnostic groups (Skoog et al., 2003); moreover, in all of these studies; Tau and Aβ42 CSF levels individually did not meet the sensitivity or specificity criteria. Further, increased levels of p-Tau have been reported in MCI and AD cases (Zetterberg et al., 2003; Herukka et al., 2005; Buerger et al., 2006; Parnetti et al., 2006). Recent studies did show improved sensitivity and specificity that met or exceeded the criteria for AD detection. The most recent report using a large number of samples with a multiplex immunoassay for measuring the CSF profile for total tau, p-Tau (threonine 181), and Aβ42 achieved 96.4% detection sensitivity for autopsy-confirmed AD (Shaw et al., 2009). This study and two others also identified that increased levels of total Tau and p-tau, decreased Aβ42, and the apolipoprotein E gene (APOE) ε4 allele as the CSF biomarker signature of autopsy-confirmed AD. This CSF signature appears to predict conversion from MCI to AD, but did not meet the criteria for correctly diagnosing MCI and predicting preclinical AD cases (Shaw et al., 2009; Li et al., 2007; Blom et al., 2009). Surprisingly, elevated levels of total and p-Tau (threonine 181) were found in the CSF of familial Alzheimer disease (FAD) mutation carriers (presenilin-1 and APP); these levels were reported as a sensitive indicator of presymptomatic AD. These authors also demonstrated that the levels of Aβ in the CSF are not a reliable biomarker for MCI or presymptomatic AD (Ringman et al., 2008).

In TBI animal models, cleaved Tau (c-Tau), phosphorylated Tau (p-tau), and total Tau (t-Tau) have been observed at increased levels in as little as 1 to 6 hours after a TBI event. Increased levels of Tau in CSF from patients with traumatic brain injury have also been observed and are closely linked to axonal injury (as reviewed in Tsitsopoulos and Marklund, 2013). In studies of milder forms of TBI, Tau levels have been slightly increased or unchanged (as reviewed in Tsitsopoulos and Marklund, 2013). In certain aspects, tau specific oligomer antibodies can be administered to a subject suspected of experience TBI in the absence of increased levels of Tau in the CSF as a prophylactic measure.

V. PROTEINACEOUS COMPOSITIONS

Proteins of the invention (e.g., the various isoforms of tau, Tau oligomers, and polypeptides that specifically bind or recognize Tau oligomers) may be recombinant, or synthesized in vitro. Alternatively, a non-recombinant or recombinant protein may be isolated from bacteria or from an organ, e.g., brain. The term "functionally equivalent codon" is used herein to refer to codons that encode the same amino acid, such as the six codons for arginine or serine, and also refers to codons that encode biologically equivalent amino acids (see below).

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of protein activity. The addition of terminal sequences particularly applies to nucleic acid sequences that may, for example, include various non-coding sequences flanking either of the 5' or 3' portions of the coding region.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules (e.g., antigenic determinants or epitopes). Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

It is contemplated that in compositions of the invention, there is between about 0.001 μg or mg and about 10 μg or mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 μg or mg/ml or more, including all values and ranges there between. Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be a Tau oligomer or an antibody that binds a Tau oligomers.

A. Polypeptides and Polypeptide Production

The present invention describes polypeptides, peptides, proteins, and segment and fragments thereof for use in various embodiments of the present invention. For example, specific antibodies are assayed for specific binding Tau oligomers. In certain embodiments, all or part of the proteins of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence which encodes a peptide or polypeptide of the invention is inserted into an expression vector, transformed or transfected into an appropriate host cell and cultivated under conditions suitable for expression. Soluble Tau proteins, amyloid polypeptide, and antibodies or segments of antibodies can be produced recombinantly.

One embodiment of the invention includes the use of gene transfer to cells, including microorganisms, for the production and/or presentation of proteins. The gene for the protein of interest may be transferred into appropriate host cells followed by culture of cells under the appropriate conditions. A nucleic acid encoding virtually any polypeptide described herein may be employed. The generation of recombinant expression vectors, and the elements included therein, are known to those of skill in the art of molecular biology. Alternatively, the protein to be produced may be an isolated endogenous protein normally synthesized by a cell.

In certain aspects an immunogenic composition according to the invention comprises a protein which has at least 85% identity, at least 90% identity, at least 95% identity, or at least 97-99% identity, including all values and ranges there between, to a Tau polypeptide (SEQ ID NO:1-6) or segment thereof.

As discussed above, the compositions and methods of using these compositions can be used in treating a subject (e.g., reducing or ameliorating a symptom of tauopathy) having, suspected of having, or at risk of developing a tauopathy or related disease. One use of the immunogenic compositions of the invention is to prophylactically treat a subject in early stages of a tauopathy by inoculating a subject, particularly once a risk of developing a tauopathy has been indicated. In certain aspects a subject may be suspected of having a tauopathy due to symptoms being presented or having a familial history of a tauopathy, i.e. genetic predisposition.

As used herein the phrase "immune response" or its equivalent "immunological response" refers to a humoral (antibody mediated), cellular (mediated by antigen-specific T cells or their secretion products) or both humoral and cellular response directed against a protein, peptide, or polypeptide of the invention in a subject or a donor subject. A donor subject is one in which an antibody is generated and isolated, the isolated antibody is then administered to a second subject. Treatment or therapy can be an active immune response induced by administration of immunogen or a passive therapy effected by administration of antibody, antibody containing material, or primed T-cells.

As used herein "passive immunity" refers to any immunity conferred upon a subject by administration of immune effectors including cellular mediators or protein mediators (e.g., monoclonal and/or polyclonal antibodies). A monoclonal or polyclonal antibody composition may be used in passive immunization for the treatment of a tauopathy or related disorder. An antibody composition may include antibodies that bind specifically to Tau oligomers. The antibody component can be a polyclonal antiserum. In certain aspects the antibody or antibodies are affinity purified from an animal or second subject that has been challenged with an antigen(s).

Passive immunity may be imparted to a patient or subject by administering to the patient immunoglobulins (Ig) or segments thereof and/or other immune factors obtained from a donor or other non-patient source having a known immunoreactivity. In other aspects, an antigenic composition of the present invention can be administered to a subject who then acts as a source or donor for globulin, produced in response to challenge from the composition ("hyperimmune globulin"), that contains antibodies directed against Tau oligomers. A subject thus treated would donate plasma from which hyperimmune globulin would then be obtained, via conventional plasma-fractionation methodology, and administered to another subject in order to impart resistance against or to treat a tauopathy. See U.S. Pat. Nos. 6,936,258, 6,770,278, 6,756,361, 5,548,066, 5,512,282, 4,338,298, and 4,748,018, each of which is incorporated herein by reference in its entirety, for exemplary methods and compositions related to passive immunity.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include those methods described in Epitope Mapping Protocols (1996). T cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., 1994), by antigen-dependent killing (cytotoxic T lymphocyte assay, Tigges et al., 1996) or by cytokine secretion.

The presence of a cell-mediated immunological response can be determined by proliferation assays (CD4 (+) T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic subject and measuring protective or therapeutic effect in a second subject.

As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM and related proteins. Antibodies of the IgG class are made up of four polypeptide chains linked together by disulfide bonds. The four chains of intact IgG molecules are two identical heavy chains referred to as H-chains and two identical light chains referred to as L-chains.

In order to produce polyclonal antibodies, a host, such as a rabbit or goat or human, is immunized with the antigen or antigen segment, generally with an adjuvant and, if necessary, coupled to a carrier. Antibodies to the antigen are subsequently collected from the sera of the host. The polyclonal antibody can be affinity purified against the antigen rendering it monospecific.

In order to produce monoclonal antibodies, hyperimmunization of an appropriate donor, generally a mouse, with the antigen is undertaken. Isolation of splenic antibody producing cells is then carried out. These cells are fused to a cell characterized by immortality, such as a myeloma cell, to provide a fused cell hybrid (hybridoma) which can be maintained in culture and which secretes the required monoclonal antibody. The cells are then cultured, in bulk, and the monoclonal antibodies harvested from the culture media for use. By definition, monoclonal antibodies are specific to a single epitope (e.g., Tau oligomers). Monoclonal antibodies often have lower affinity constants than polyclonal antibodies raised against similar antigens for this reason.

Monoclonal antibodies may also be produced ex vivo by use of primary cultures of splenic cells or cell lines derived from spleen (Anavi, 1998). In order to produce recombinant antibody (see generally Huston et al., 1991; Johnson et al., 1991), messenger RNAs from antibody producing B-lymphocytes of animals, or hybridoma are reverse-transcribed to obtain complementary DNAs (cDNAs). Antibody cDNA, which can be full length or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

As used herein and in the claims, the phrase "an immunological portion of an antibody" include a Fab fragment of an antibody, a Fv fragment of an antibody, a heavy chain of an antibody, a light chain of an antibody, an unassociated mixture of a heavy chain and a light chain of an antibody, a heterodimer consisting of a heavy chain and a light chain of an antibody, a catalytic domain of a heavy chain of an antibody, a catalytic domain of a light chain of an antibody, a variable fragment of a light chain of an antibody, a variable fragment of a heavy chain of an antibody, and a single chain variant of an antibody, which is also known as scFv. In addition, the term includes chimeric immunoglobulins which are the expression products of fused genes derived from different species, one of the species can be a human, in which case a chimeric immunoglobulin is said to be humanized. Typically, an immunological portion of an antibody competes with the intact antibody from which it was derived for specific binding to an antigen.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

A method of the present invention includes treatment for a tauopathy or condition caused by a Tau oligomers. Furthermore, in some examples, treatment comprises administration of other agents commonly used to treat tauopathies.

The therapeutic compositions are administered in a manner compatible with the dosage formulation, and in such amount as will be therapeutically effective. The quantity to be administered depends on the subject to be treated. Precise amounts of active ingredient required to be administered depend on the judgment of the practitioner. Suitable regimes for initial administration and boosters are also variable, but are typified by an initial administration followed by subsequent administrations.

The manner of application may be varied widely. Any of the conventional methods for administration of a polypeptide therapeutic are applicable. These are believed to include oral application on a solid physiologically acceptable base or in a physiologically acceptable dispersion, parenterally, by injection and the like. The dosage of the composition will depend on the route of administration and will vary according to the size and health of the subject.

In certain instances, it will be desirable to have multiple administrations of the composition, e.g., 2, 3, 4, 5, 6 or more administrations. The administrations can be at 1, 2, 3, 4, 5, 6, 7, 8, to 5, 6, 7, 8, 9, 10, 11, 12 twelve week intervals, including all ranges there between.

B. Antibodies and Passive Immunization

Certain aspects are directed to methods of preparing an antibody for use in prevention or treatment of a tauopathy comprising the steps of administering a recipient with a Tau oligomer and isolating antibody from the recipient, or producing a recombinant antibody. An antibody prepared by these methods and used to treat or prevent a tauopathy are a further aspect of the invention. A pharmaceutical composition comprising antibodies that specifically bind a Tau oligomer and a pharmaceutically acceptable carrier is a further aspect of the invention which could be used in the manufacture of a medicament for the treatment or prevention of a tauopathy.

Inocula for polyclonal antibody production are typically prepared by dispersing the antigenic composition (e.g., a Tau oligomer) in a physiologically tolerable diluent such as saline or other adjuvants suitable for human use to form an aqueous composition. An immunostimulatory amount of inoculum is administered to a mammal and the inoculated mammal is then maintained for a time sufficient for the antigenic composition to induce protective antibodies. The antibodies can be isolated to the extent desired by well known techniques such as affinity chromatography (Harlow and Lane, 1988). Antibodies can include antiserum preparations from a variety of commonly used animals e.g., goats, primates, donkeys, swine, horses, guinea pigs, rats or man. The animals are bled and serum recovered.

An antibody produced in accordance with the present invention can include whole antibodies, antibody fragments/segments or subfragments. Antibodies can be whole immunoglobulins of any class (e.g., IgG, IgM, IgA, IgD or IgE), chimeric antibodies, human antibodies, humanized antibodies, or hybrid antibodies with dual specificity to two or more antigens. They may also be fragments (e.g., F(ab')2, Fab', Fab, Fv and the like including hybrid fragments). An antibody also includes natural, synthetic or genetically engineered proteins that act like an antibody by binding to specific antigens with a sufficient affinity.

A Tau oligomer of the present invention can be administered to a recipient who then acts as a source of antibodies, produced in response to challenge from the Tau oligomer. A subject thus treated would donate plasma from which antibody would be obtained via conventional plasma fractionation methodology. The isolated antibody would be administered to the same or different subject in order to impart resistance against or treat a tauopathy.

An additional aspect of the invention is a pharmaceutical composition comprising one of more antibodies or monoclonal antibodies (or fragments thereof; preferably human or humanized) reactive against Tau oligomers.

Methods of making monoclonal antibodies are well known in the art and can include the fusion of splenocytes with myeloma cells (Kohler and Milstein, 1975; Harlow and Lane, 1988). Alternatively, monoclonal Fv fragments can be obtained by screening a suitable phage display library (Vaughan et al., 1998). Monoclonal antibodies may be humanized or part humanized by known methods.

C. Combination Therapy

The compositions and related methods of the present invention, particularly administration of Tau oligomers or an antibody that binds Tau oligomers to a patient/subject, may also be used in combination with the administration of traditional therapies. These include, but are not limited to, (1) interference with the splicing machinery to decrease the four-repeat Tau isoforms, (2) activation of proteolytic or proteasomal degradation pathways, (3) prevention/reduction of Tau hyperphosphorylation using inhibitors of Tau kinases, (4) pharmacological stabilization of microtubule networks, (5) inhibition of Tau aggregation by small molecules, and (6) tau-directed immunotherapy.

In one aspect, it is contemplated that a traditional therapy is used in conjunction with a Tau oligomer or Tau oligomer specific antibody treatment. Alternatively, the therapy may precede or follow the traditional therapy by intervals ranging from minutes to weeks. In embodiments where the other agents and/or a proteins or polynucleotides are administered separately, one would generally ensure that a significant period of time did not expire between the time of each delivery, such that the therapeutic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Various combinations of therapy may be employed, for example Tau oligomer or Tau oligomer specific antibody therapy is "A" and a traditional tauopathy therapy is "B". These combinations can include A followed by various combinations and permutations A and B, or can include B followed by various combinations and permutations A and B.

Administration of the antibody compositions of the present invention to a patient/subject will follow general protocols for the administration of such compounds, taking into account the toxicity, if any, of the composition. It is expected that the treatment cycles would be repeated as necessary. It is also contemplated that various standard therapies, such as hydration, may be applied in combination with the described therapy.

Inhibition of Tau Hyperphosphorylation.

This approach to treat AD was first introduced in 1998 (Gong and Iqbal, 2008). Although a kinase inhibitor was shown to reduce Tau hyperphosphorylation and the formation of soluble aggregated Tau and to prevent motor deficits in mice expressing mutant human Tau (Iqbal and Grundke-Iqbal, 1998), a major drawback to targeting kinases is that these enzymes are commonly found throughout the body playing normal physiological roles and their inhibition may have unwanted side effects.

Activation of Proteolytic or Degradation Pathway.

Tau was found to be sensitive to calpain proteolysis (Johnson et al., 1989). Recently, puromycin-sensitive aminopeptidase (PSA), which was identified by a genetic screen as a modifier of Tau pathology (Sengupta et al., 2006), was shown to be effective in degrading both recombinant and PHF Tau purified from AD brain (Karsten et al., 2006).

Stabilization of Microtubules.

Microtubule-binding drugs that could be beneficial in treating tauopathies by functionally substituting for the MT-binding protein Tau (Trojanowski et al., 2005). Paclitaxel, a drug know to bind and stabilize microtubules, was tested in transgenic mice and showed to be effective in restoring axonal transport and ameliorating motor impairments (Zhang et al., 2005).

Inhibition of Tau Aggregation by Small Molecules.

The last decade has witnessed a renaissance of interest in inhibitors of Tau aggregation as potential disease-modifying drugs. The search for non-toxic, cell penetrant inhibitors of Tau aggregation capable of crossing the blood-brain barrier (BBB) was performed using a high throughput screen, which resulted in the identification of more than 139 hits (Pickhardt et al., 2005; Larbig et al., 2007). This and the recent report of a phase-II clinical trial with the Tau aggregation inhibitor MTC (ma ethylene blue derivative) could hold promise for the validation of this concept. The research on Tau aggregation inhibitors was recently review (Bulic et al., 2009).

Tau Clearance by Immunotherapy.

A novel study used active immunization with a phosphorylated Tau epitope in mice expressing Tau with the P301L mutation showed reduction of aggregated Tau in the brain and slowed progression of the behavioral phenotype. Moreover, this study demonstrated that antibodies against the immunogen used can cross the BB and bind to phosphorylated Tau (Asuni et al., 2007).

VI. THERAPEUTIC USE OF TAU AND TOMA COMPOSITIONS

The body of evidence supporting an important role of Tau in neurodegenerative diseases (Ballatore et al., 2007; Haroutunian et al., 2007) supports Tau as a potential target for the development of disease modifying therapeutics. Therapeutic approaches targeting Tau include, (1) interference with the splicing machinery to decrease the four-repeat Tau isoforms, (2) activation of proteolytic or proteasomal degradation pathways, (3) prevention/reduction of Tau hyperphosphorylation using inhibitors of Tau kinases, (4) pharmacological stabilization of microtubule networks, (5) inhibition of Tau aggregation by small molecules, and (6) tau-directed immunotherapy (Schneider and Mandelkow, 2008). Aspects of the present invention include antibody-based methods and peptide based methods for the treatment of tauopathies.

The correlation between NFT in the brains of AD patients with the disease progression remains contentious (Bretteville and Planel, 2008; Braak and Braak, 1991; Delacourte and Buee, 2000; Morsch et al., 1999; Congdon and Duff, 2008; Arriagada et al., 1992 Bird et al., 1999; Hernandez and Avila, 2008; Tabaton et al., 1989; Cash et al., 2003). In the last half decade, data are emerging from biochemical, cell-based and transgenic mouse studies that suggest that prefilament forms of Tau may be the most toxic and pathologically significant form of Tau aggregates (Brunden et al., 2008; Marx, 2007). This evolutionary transition was overdue in the Tau field and similar to the transition witnessed for Aβ in the last 15 years driven by the characterization of Aβ intermediate species and their crucial role in Aβ-mediated toxicity (Harper et al., 1997; Roher et al., 1993; Walsh and Selkoe, 2004; Walsh and Selkoe, 2007).

Analogous to Aβ oligomers, Tau oligomers have been shown to be neurotoxic when applied extracellularly to cultured neuronal cells and to provoke an increase in intracellular calcium levels (Demuro et al., 2005; Gomez-Ramos et al., 2006; Gomez-Ramos et al., 2008) Innovative work using animal models suggests that Tau oligomers play a key role in eliciting neurodegeneration and behavioral impairments. These phenotypes are concurrent with accumulation of soluble aggregated Tau species and dissociated from the accumulation of NFT (Brunden et al., 2008). Cell death occurred independently of NFT formation in aged (h-Tau mice) expressing non-mutant human Tau (Andorfer et al., 2005); hippocampal synapse loss, impaired synaptic function and microgliosis precede the formation of NFT in the P301S mutant human Tau transgenic mouse model (P301S Tg) (Yoshiyama et al., 2007). Tau oligomers were biochemically characterized in the JNPL3 mice expressing human Tau with the P301L mutation, and the conditional model (rTg4510) expressing the same P301L human Tau mutant; surprisingly, the accumulation of oligomeric Tau correlated best with neuronal loss and behavioral deficits in these models, whereas NFT did not. These findings suggest that the accumulation of Tau oligomers, behavioral deficits and neuronal loss precede the formation NFT (Berger et al., 2007; Spires et al., 2006).

Tau oligomers have been biochemically characterized in post mortem human brain, and a correlation between disease progression and the accumulation of granular Tau oligomers in the brains of AD patients was reported. Moreover, increased levels of Tau oligomers detected in the frontal cortex at very early stage of the disease (Braak stage I), when clinical symptoms of AD and NFT are believed to be absent. This finding suggests that an increase in Tau oligomer levels occurs before NFT formation and before individuals manifest clinical symptoms of AD (Maeda et al., 2007; Maeda et al. 2006). Tau-positive fine granules (TFGs) resembling Tau oligomers were found in the cerebral white matter of post mortem tissue from the parkinsonism-dementia complex of guam (PDC) tauopathy (Yamazaki et al., 2005).

The data discussed here support the notion that soluble oligomers of amyloid proteins including Tau are the acutely toxic structures of these proteins, rather than insoluble aggregates like plaques and tangles. This concept has become more generally accepted for multiple neurodegenerative diseases including AD and tauopathies (Brunden et al., 2008; Haass and Selkoe, 2007). The resurgence of Tau and Tau oligomers in particular as a potential drug target to combat neurodegeneration (Marx, 2007) led to studies to identify specific reagents to study and target Tau oligomers in AD brain and animal models. The studies described herein indicate that Tau oligomers are the pathological form of Tau and should be exclusively targeted without interfering with soluble functional Tau or the non-toxic NFT. The methods and reagents described herein bypass the disadvantages associated with targeting all forms of Tau indiscriminately. The specific reagents described unexpectedly associate Tau oligomers with AD and tauopathies. Thus, while Tau oligomers may exert general toxic effects in many diseases, they present a novel target for drug development to treat several diseases, and their quantification can serve as reliable biomarker.

In some embodiments, pharmaceutical compositions are administered to a subject to treat tauopathies. Different aspects of the present invention involve administering an effective amount of a composition to a subject. In some embodiments of the present invention, Tau oligomers or Tau oligomer specific antibody may be administered to the patient to treat a tauopathy. Alternatively, an expression vector encoding one or more such antibodies or polypeptides or peptides may be given to a patient as a treatment. Such compositions will generally be dissolved or dispersed in a pharmaceutically acceptable carrier or aqueous medium. The phrases "pharmaceutically acceptable" or "pharmacologically acceptable" refer to molecular entities and compositions that do not produce an adverse, allergic, or other untoward reaction when administered to an animal or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-infective agents and vaccines, can also be incorporated into the compositions.

The active compounds of the present invention can be formulated for parenteral administration, e.g., formulated for injection via the intravenous, intramuscular, subcutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization or an equivalent procedure. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions according to the present invention will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain aspects a Tau oligomer specific antibody can be administered into the cerebrospinal fluid of the brain or spine. In certain embodiments, a Tau oligomer composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above. In certain aspects, the subject is treated within at least 1 hr, within at least 2 hr, within at least 4 hr, within at least 6 hr, within at least 8 hr, within at least 10 hr, within at least 12 hr, within at least 14 hr, within at least 16 hr, within at least 18 hr, within at least 20 hr, within at least 22 hr, or within at least 24 hr of suffering the traumatic brain injury. In some embodiments, the subject is treated for at least 7 days, at least 14 days, or at least 28 days after suffering the traumatic brain injury.

VII. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Methods and Uses of a Homogeneous Population of Tau Oligomers a Novel Anti Tau Oligomer Polyclonal Antibody (T2286).

Figures 3A, 3B:
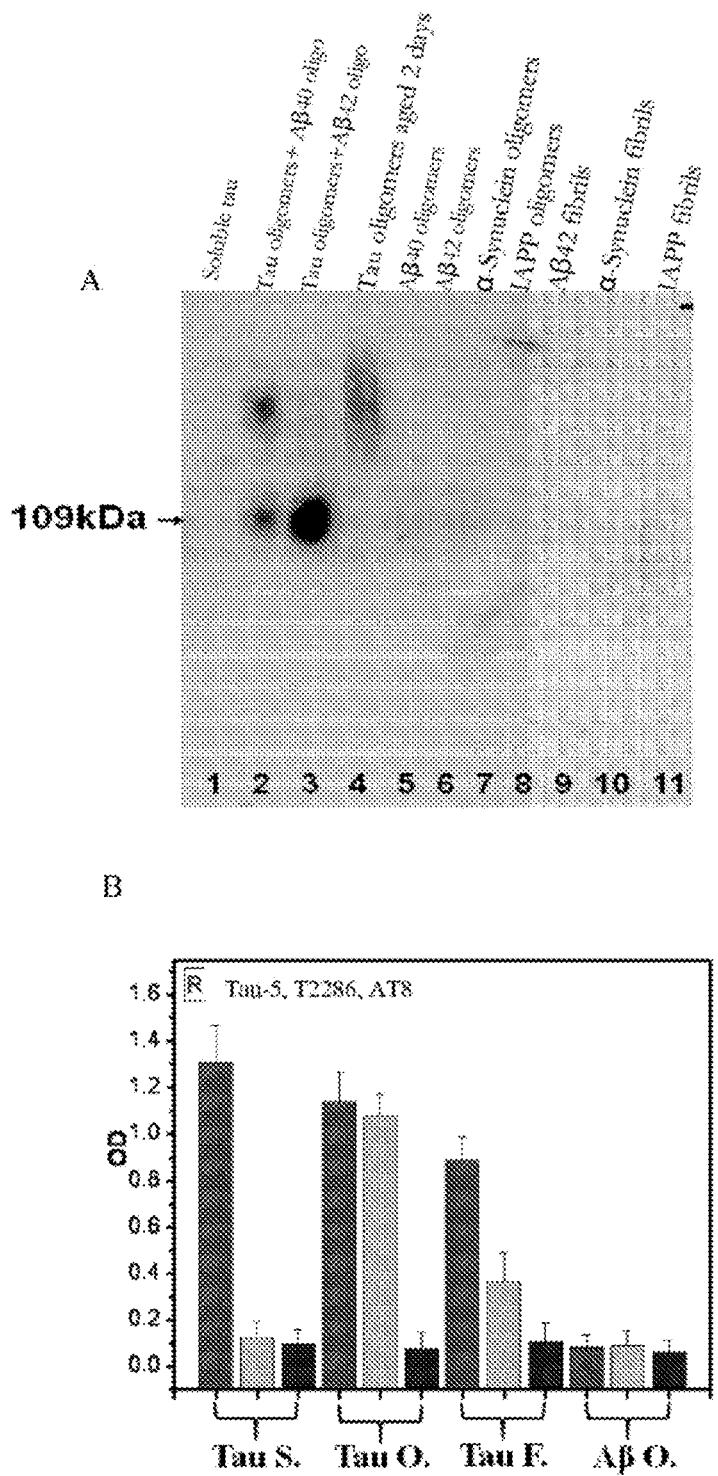
FIGS. 3A-3B. T2286 (Novel tau oligomer specific antibody) detects only tau oligomers but not monomeric tau or tau fibrils; moreover, it does not detect oligomers from other proteins. (A) WB using T2286: (1) Tau monomer. (2) tau oligomers+Aβ40 oligomers, (3) tau oligomers+Aβ42 oligomers. (4) tau oligomers (same as 3) aged 2 days at R.T (5) Aβ40 oligomers. (6) Aβ42 oligomers. (7) α-synuclein oligomers. (8) IAPP oligomers. (9) Aβ42 fibrils. (10) α-synuclein fibrils (11) IAPP fibrils. (B) T2286 specificity was confirmed by (ELISA). T2286 reacts specifically with tau oligomers; no reactivity with monomeric tau or tau fibrils; nor is there any reactivity with Aβ oligomers.
Figure 7:
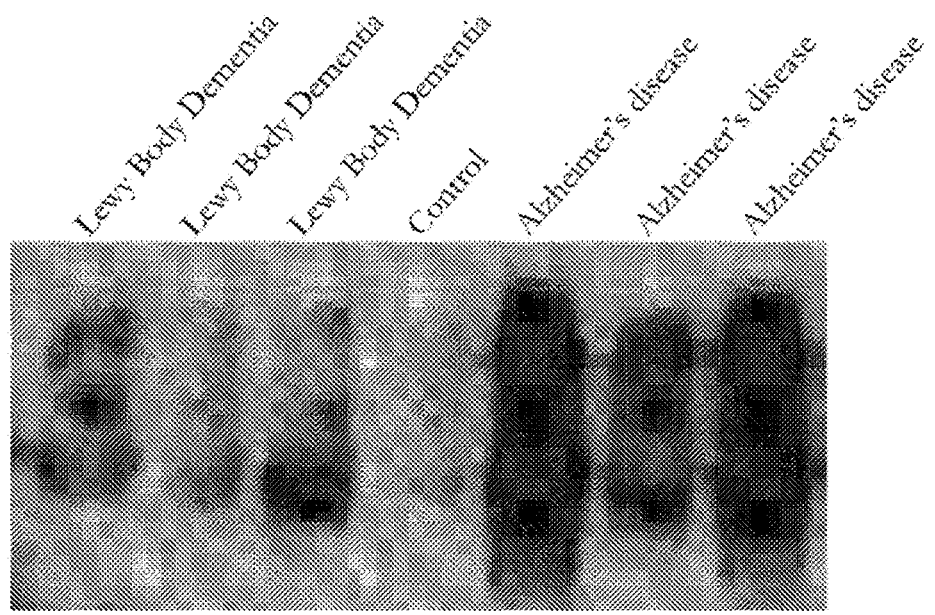
FIG. 7. Detection of Tau oligomers in Lewy Body Dementia (LBD) and Alzheimer's Disease (AD) samples using the T2286 antibody composition. T2286; recognizes oligomeric tau in immunoblots of LBD cortex, these oligomers were similar to the ones found in AD brains.
Figure 8:
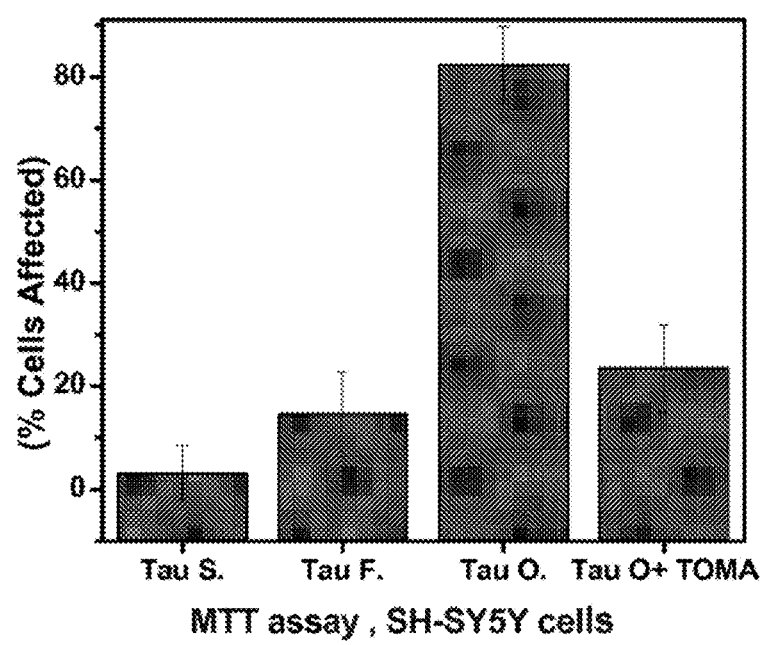
FIG. 8. Tau oligomer monoclonal antibodies (TOMA) reduces Tau oligomer toxicity. Tau oligomers are toxic, tested in SY5Y cells. The toxicity can be prevented by TOMA 1-Tau monomer; 2-Tau fibrils; 3-Tau oligomers 4-Tau oligomer+TOMA.
Figure 9:
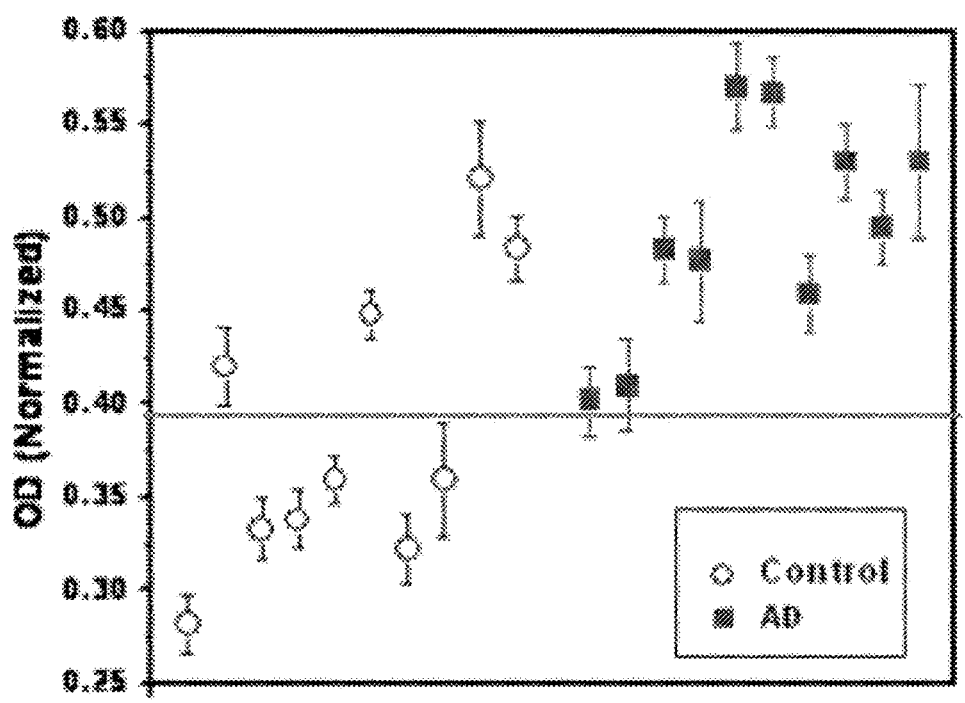
FIG. 9. Tau oligomers are detected in cerebral-spinal fluid (CSF) of AD patients.

Immunogenicity of the homogenous population of Tau oligomers was exploited to generate antibodies specific for Tau oligomers. Rabbits were vaccinated with 0.25 mg of Tau oligomers and then boosted 3 times at two weeks intervals. The serum was collected and its reactivity with all forms of Tau and other amyloids was evaluated using pre-immune serum as control. A novel anti Tau oligomer antibody (T2286) was obtained. This novel antibody specifically recognizes Tau oligomers but does not react with soluble or fibrillar tau. Unlike the anti-oligomer antibodies generated in the past, A-11 and 1-11, T2286 reacts only with Tau oligomers, not with oligomers prepared from any other protein (FIG. 3). T2286 can be describes as a sequence conformation antibody not a conformation antibody. The smallest Tau species recognized by T2286 on western is probably a trimer (110-120 KDa); this species is transient in nature and converts to larger aggregates with time (FIG. 3). Moreover, T2286 binding to Tau oligomers eliminates their toxicity (FIG. 7 A).

Tau oligomers in AD brain analyzed using T2286 was motivated by the surprising results obtained from testing in vitro samples. T2286 was used to detect Tau oligomers in brain samples. The preliminary data from the biochemical analysis of AD brains and age matched controls showed elevated levels of Tau oligomers in the PBS soluble fraction (FIG. 4) and the Triton soluble fraction (data not shown). No Tau oligomers were detected in the formic acid soluble fraction or the triton insoluble fraction. Moreover, preliminary data suggest that the majority of Tau oligomers in AD brain are unphosphorylated, based on western blot and ELISA analysis using T2286 and AT8 (data not shown). The preliminary data from immunohistochemical analysis of AD showed the presence of Tau oligomers both intra- and extracellularly (data not shown) and very little overlap with both AT8 and PHF-1 confirming the results obtained from the biochemical analysis. Interestingly, Tau oligomers in AD brain were heavily ubiquitinated (data not shown), suggesting that Tau oligomers may play a role in have role in the proteasomal dysfunction in AD.

Tau Oligomers in CSF Analyzed Using T2286.

The levels of both total Tau (t-tau) and phosphorylated Tau specially (p-tau-threonine 181) were found to be elevated in the CSF. A pilot experiment was performed using T2286 to measure Tau oligomers in CSF samples from AD and controls patients by direct ELISA. T2286 largely distinguished between AD and controls and outperformed AT8 and Tau5.

Tau Oligomers in Tg Mouse Models Using T2286.

Brain samples from Tg4510 were analyzed, the P301L animals were provided by Dr. Karen Ashe, University of Minnesota. Animal at ages 2, 5, 6, 8, 10 and 11 months were analyzed using the biochemical and immunohistochemical analysis describe above. The results showed a correlation between the presence of Tau oligomers and phenotypes for this model and confirmed published reports describing the formation of Tau oligomers in this model with similar molecular weight to the oligomers detected by T2286. Tau oligomers were also detected in APP/PS-1 mice and other animal models of tauopathies (data not shown).

Tau Oligomer Monoclonal Antibody (TOMA).

While rabbit polyclonal antibodies like T2286 are useful for research, their potential for vaccine development is limited. The data described here prompted the production of monoclonal anti Tau oligomers antibodies (TOMA) using the same antigen described above. For the production standard protocols were used. Screening for TOMA proved challenging; an elaborate screening protocol was used—the screen produced more than thirteen TOMA clones specific for Tau oligomers (including TOMA-1 (clone H12C10 an IgG2a), TOMA-2 (clone B3E7 an IgG1) and TOMA-3 (F3D4 an IgG2a), similar to the specificity described for T2286; moreover the monoclonal antibodies have higher affinity toward Tau oligomers. TOMA clone F3D4 was produced in large quantities. Using TOMA the inventor was able to replicate data generated using T2286. Some of the results obtained using TOMA are described below, including preliminary data from AD brain samples and mouse brains from different models of AD and tauopathy. These results confirmed that TOMA-F3D4 is an anti-tau oligomer specific antibody.

Tau Oligomers in Transgenic Mouse Models Using TOMA.

Using TOMA, the brains from Tg4510 at 2 and 5 months were analyzed, biochemically elevated levels of Tau oligomers were found at 5 moths compared to 2 months old (data not shown) Tau oligomers were also detectable by IHC; brain from the APP/PS-1 at 3 months old was also analyzed, Tau oligomers were detected.

Tau Oligomers in AD Brain Using TOMA.

Figures 4A, 4B:
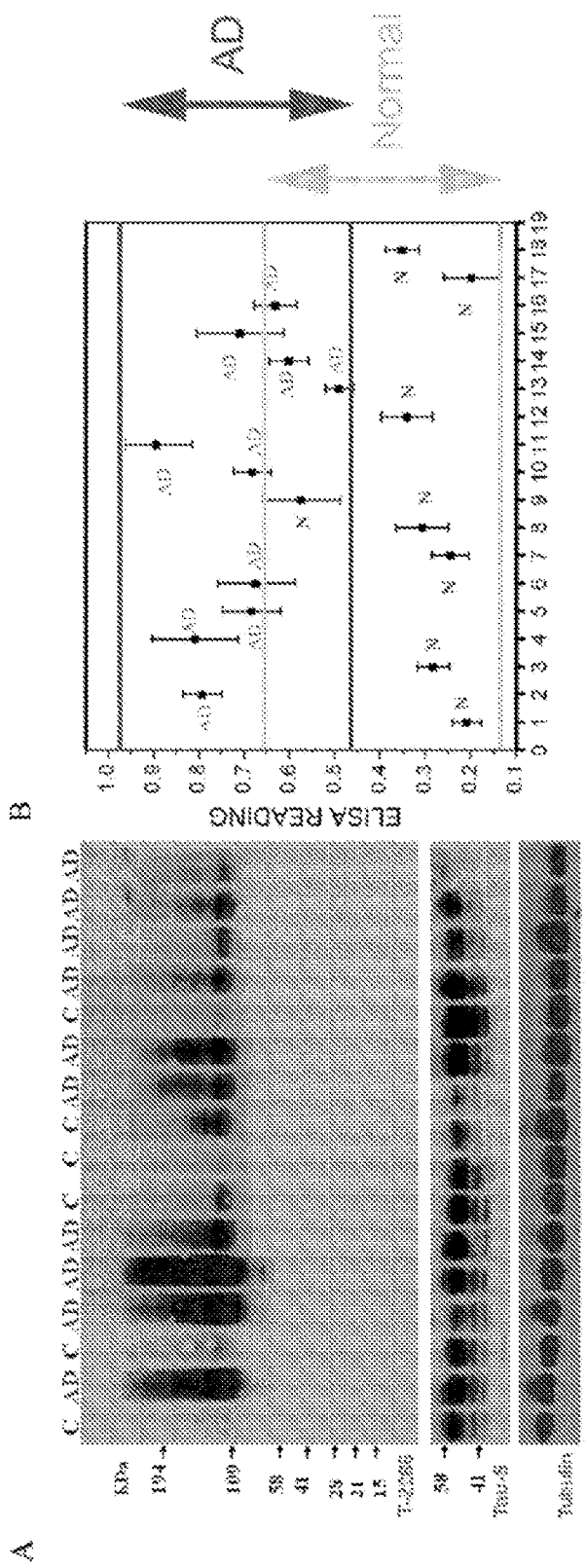
FIGS. 4A-4B. Tau oligomers in AD patients. (A) Western blot of PBS soluble fraction from AD & control brain samples (frontal cortex). It is clear that tau oligomers detected by T-2286 are elevated in AD brain (red) compared to control brain (blue), it is clear that T-2286 doesn't recognize monomeric tau. (B) Tau oligomers levels were elevated in the CSF from AD patients vs. controls, Measured by direct ELISA using 50 µl of CSF.
Figures 5A, 5B, 5C, 5D, 5E:
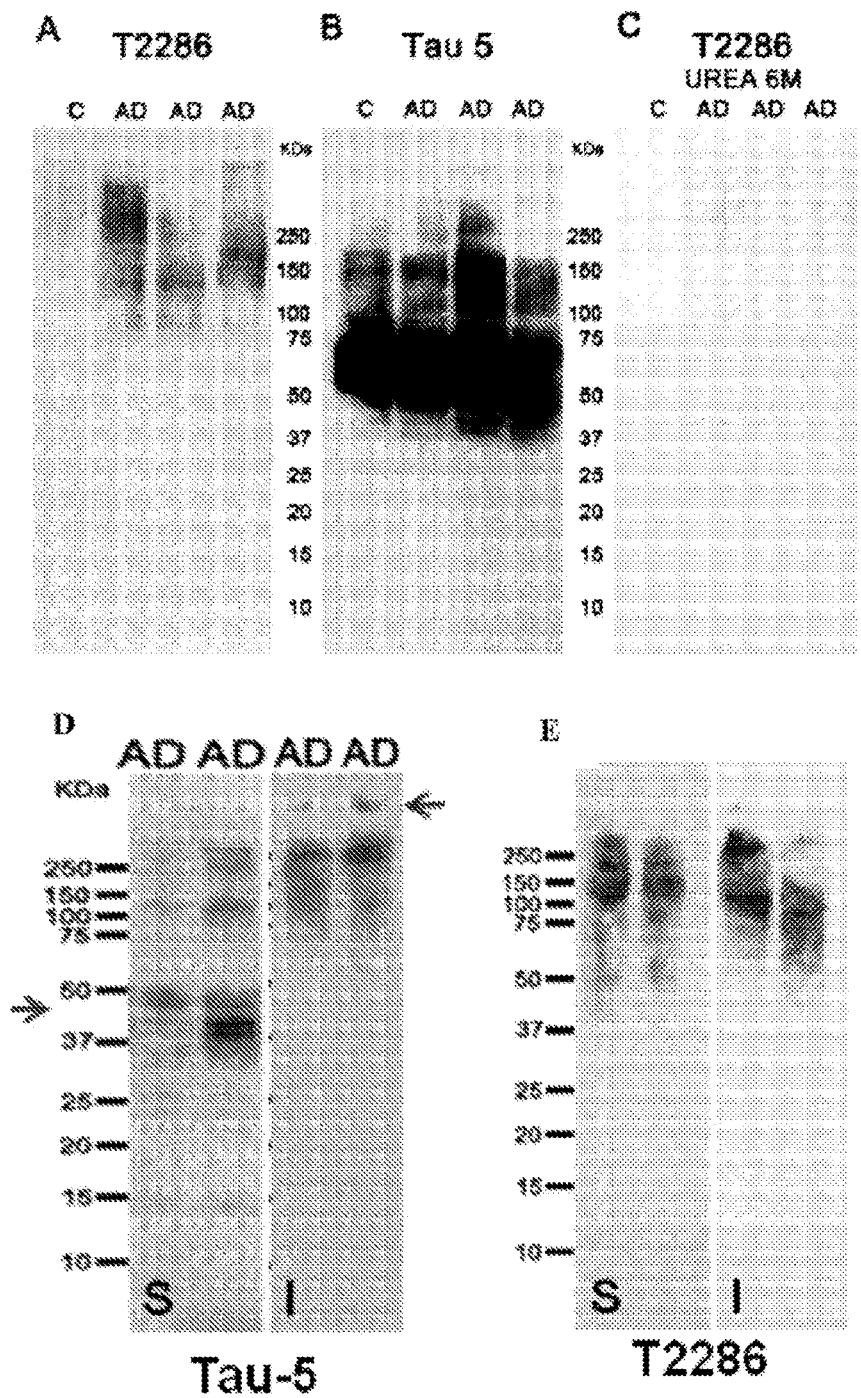
FIGS. 5A-5E. T2886 detects tau oligomers in the PBS fraction of AD brains (A) T2886 only recognizes higher molecular weight species and not monomer. (B) Tau 5 detects total tau including the monomer. (C) To determine the conformational specificity of T2286, almost no signal was detected after urea treatment. Tau oligomers were found in both sarkosyl soluble (S) and insoluble (I) fractions (29). Tau monomer recognized by Tau 5 in the soluble fraction (left arrow) or the NFT in the insoluble fraction (right arrow) (D), is not recognized by T2286 (E).
Figure 6:
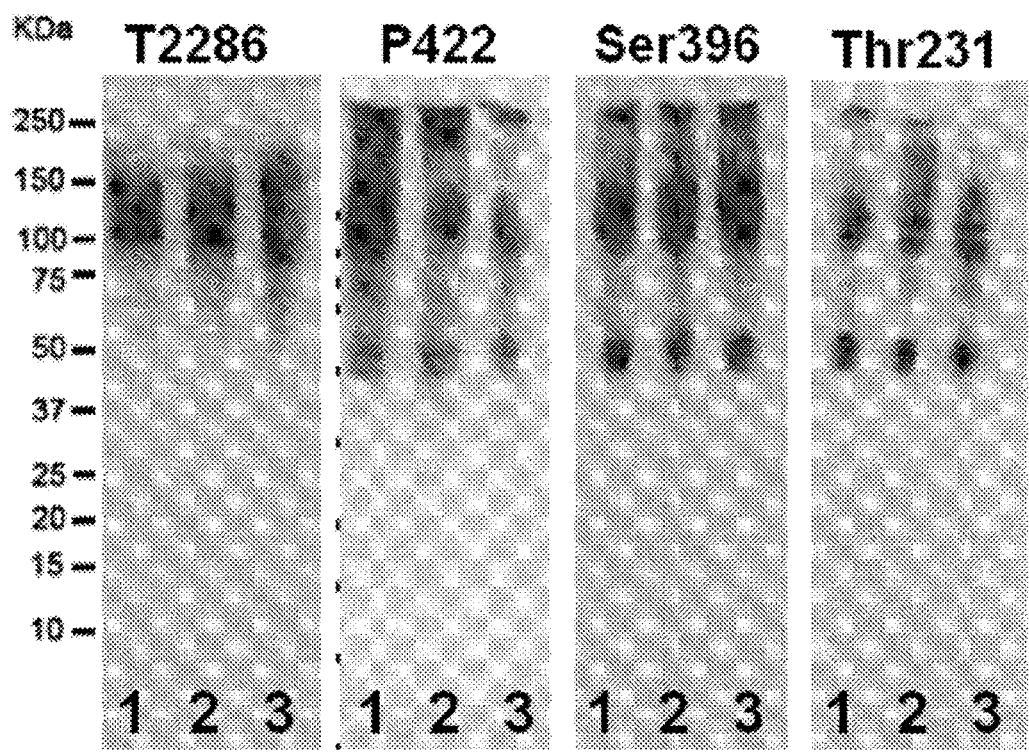
FIG. 6. Biochemical analysis of Tau oligomers. Alkaline phosphatase has a limited effect on tau oligomer from AD brain as assessed by T2285 signal as compared using 3 phosphoepitopes. PBS brain homogenates analyzed by WB, (1) untreated, (2) treated with 400 U/ml, (3) treated with 800 U/ml phosphatase.

Tau oligomers in AD brain were characterized using TOMA. Data using TOMA in combination with other well characterized antibodies revealed elevated levels of Tau oligomers in AD brains compared to age-matched controls, and demonstrated the presence of Tau oligomers both intracellularly and extracellularly in AD brains (FIG. 4).

Example 2

Material and Methods for Making and Using Tau Oligomers

One aspect of these studies is to use anti Tau oligomer monoclonal antibodies to elucidate the role of Tau oligomers and evaluate the benefits of their clearance by passive vaccination. The vast majority of protein aggregates have been reported to be pathologically significant and to co-exist in many diseases. Although the accumulation of Tau oligomers in human brain and transgenic models has been reported, details regarding their distribution and significance in disease phenotypes remain unknown. Thus, evaluation of the role of these structures is needed. Knowledge of the detailed distribution of Tau oligomers can help in understanding the molecular mechanisms of neurodegeneration. Knowledge of the benefits of Tau oligomers clearance may help in the design and evaluation of potential therapeutic strategies to treat AD and other tauopathies.

Immunohistochemical and biochemical methods using TOMA in combination with other well characterized antibodies are used to make qualitative and quantitative analysis of the levels, localization and post translational modifications of Tau oligomers in well characterized brain samples of AD patients and age-matched controls. The inventor can quantitate Tau oligomers in a large number of CSF samples. These samples can be analyzed biochemically by direct ELISA, immunoprecipitation/western, and sandwich ELISA.

Tau oligomers can be characterize in transgenic animal models of AD and tauopathy and determine whether their accumulation correlates with the behavioral deficits. Tau oligomers can be studied in brain from the AD models Tg 2576 and APP/PS1 mice, as well as the P301L Tau (JNPL3). Brains/CNS at various ages can be analyzed using the described methods. These experiments will assess the role of Tau oligomer in disease phenotypes and will assist in the design of passive vaccinations using TOMA.

Figure 10:
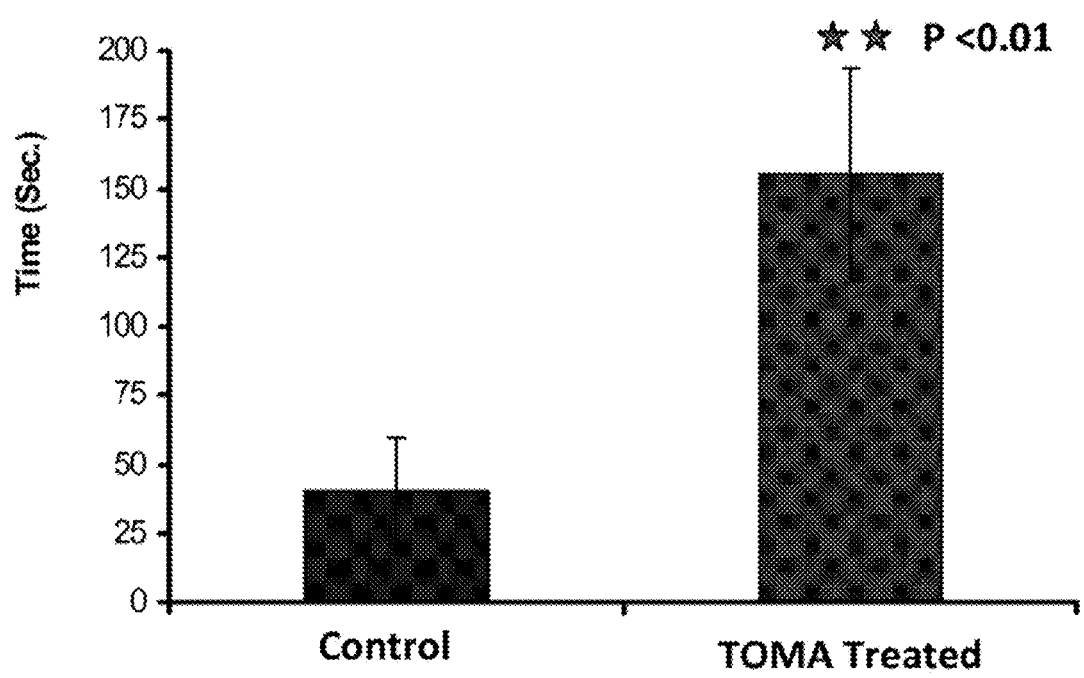

The efficacy of passive vaccination can be assessed using TOMA in transgenic mouse models. Tau oligomers can be administered to P301 L Tau (JNPL3) model of tauopathy. JNPL3 mice have been used effectively in an active vaccination study directed at targeting Tau aggregates (Asuni et al., 2007). Tg2576 mice can be administered Tau oligomers for the study of therapeutic effects of a polypeptide composition. Mice will be vaccinated at various ages, and comprehensive behavioral assessments will be performed before and after vaccination, including, fear conditioning, object recognition, locomotor activity, rotarod, and traverse beam. Additional models will be added if significant improvement is observed in both or one of these two models. These studies provide valuable information into the dynamics of Tau oligomers, assess the merit of targeting Tau oligomers solely by TOMA, and the feasibility for developing a vaccine for therapeutic purposes. FIG. 10 illustrates data that demonstrate a beneficial affect of TOMA in mouse model of neurodegeneration using a rotarod assay.

Correlation of Tau Oligomers with Pathology in AD Brain and CSF.

The presence, distribution and posttranslational modifications of Tau oligomers can be measured and analyzed in post mortem brain and CSF samples. Immunohistochemical and biochemical analyses are performed using TOMA and other available antibodies. Unlike previous studies that have focused on Tau modifications, such as truncation and site specific phosphorylation, the inventor will examine Tau oligomers burden first and then analyze its correlation with reported modification.

Immunohistochemical Analysis of Tau Oligomers in AD Brain.

The inventor describes using TOMA in combination with other well-characterized antibodies. These studies detail the multiple types of Tau aggregates present in AD brain. NFT in AD brain have been studied extensively, but data describing Tau oligomers in AD brain is unavailable, and their role has not been yet determined. The data obtained from animal models argue that the methods and compositions proposed here are useful in understand Tau oligomers in AD. IHC analysis of brain samples using TOMA in combination with Tau 5, HT7, pThr231, p422, AT100, AT8 and pSer396, produces information about tau oligomers, their phosphorylation state, and their relation with NFT. IHC experiments detail the development of the toxic tau oligomers in AD brains and unveil their role in the disease progression.

Patient and Brain Tissue Selection:

Frozen brain tissues were obtained from the Institute for Brain Aging and Dementia (UC Irvine) and the Brain Resource Center (Johns Hopkins School of Medicine). Tau pathology begins in transentorhinal cortex and progresses to the frontal cortex, based on the progression of Tau deposition over the course of the disease as described by Braak and Braak and others. Tissues are examined from transentorhinal cortex and cerebellum, entorhinal cortex, and hippocampus (Brodmann's Area's 11, 9 and 4).

Selected patients represent the spectrum seen in AD progression, and only well-characterized samples are used. Sample information should have the clinical and pathological details of the patient, and patients were matched for age, gender and post-mortem index (PMI), mini mental state examination (MMSE) score, clinical dementia rating (CDR) score and cognitive ability screening instrument (CASI) score.

Antibody Selection:

Samples are analyzed using the novel Tau oligomers monoclonal antibody TOMA and other antibodies; including A-11 and 1-11, anti-oligomer antibodies (Kayed et al., 2003; Meier et al., 2006), OC and LOC anti-fibril antibodies (Kayed et al., 2007) and Officer, an anti-annular protofibril antibody (Kayed et al., 2009). In addition, commercially available antibodies will be used as necessary: such as, Tau antibodies against neurofibrillary tangles and specific phosphor-Tau epitope, anti-Tau HT7, AT270, ATB, and AT100, Tau-5, PHF-tau, anti-Tau pS199, pS262, and pS422.

Tissue Processing:

Brain samples are fixed in a 10% neutral buffered formalin solution under standard conditions for neuropathological purposes. Samples from each brain are processed for paraffin embedding according to conventional methods and for frozen sections. The reason to work with both type of tissue preparation is that some antibodies work better in paraffin embedded sections than in frozen sections or vice versa. Furthermore, some antibodies react better with the DAB detection method, but not with fluorescent secondary antibodies or vice versa. The reactivity of TOMA on post mortem human brain tissue is evaluated empirically using varying antibody dilution and carefully control staining.

Immunohistochemistry in Paraffin Sections, and Immunofluorescence in Frozen Sections.

Working with conformational antibodies is very challenging, especially when used to detect a dynamic and most likely transient species like Tau oligomers. The protocols preserve the conformational epitope while making it accessible to the antibody. For this purpose, the protocols are optimized and tailored.

Data Analysis:

Bright-field Images are acquire using a Nikon Eclipse 800 microscope equipped with a Nikon DXM1200 color CCD camera controlled by ACT-1 acquisition software (Nikon Instruments Inc., Melville, N.Y.). The fluorescent images are examined using a confocal microscope Zeiss LSM 510 (Zeiss, Hornwood, N.Y.) equipped with three laser lines. Argon ion laser with 4 lines of excitation: 458, 477, 488, 514 nm, Green He/Ne with excitation at 543 nm and Red He/Ne with excitation at 633 nm. To quantify the immunoreactivity, the brain samples are analyzed using Stereo Investigator (MBF Bioscience, Williston, Vt.). A region of interest is outlined and the area fraction fractionator probe is used systematically and randomly, allocated sampling sites 400 µm apart. At each sampling site, 100×80 µm counting frame is superposed, containing markers equally spaced from one another at a distance of 15 µm. The markers that co-localize with TOMA immunoreactivity are labeled as positive, whereas remaining markers are labeled negative. The area fraction is calculated as the number of positive markers divided by the total number of markers. The stereological assessment is made in a blinded fashion. The statistical analysis for the area fraction of TOMA immunoreactivity is performed using one-way ANOVA followed by Bonferroni's multiple comparison test to allow for comparisons between groups. All statistical analysis is performed using GraphPad Prism version 5.00 for Windows, (GraphPad Software, San Diego, Calif.).

Quantification and statistical analysis, to quantify the immunoreactivity, the brain samples are analyzed using Stereo Investigator (MBF Bioscience, Williston, Vt.). A region of interest is outlined; the fractionator probe is used systematically and randomly, allocated sampling sites 400 µm apart. Tau rabbit antibodies such as, ab64193, and p422 are used as markers with TOMA. TOMA is labeled with the fluorophore (Alexa Fluor488), and double staining is performed in tissue sections using labeled TOMA and other mouse tau antibodies. Briefly, sections are first incubated with the commercial antibody, and then with a secondary antibody goat anti mouse label with Alexa Fluor568 and finally sections are incubated with TOMA label with Alexa Fluor488. For analysis, each sampling site, a 100×80 µm counting frame is superposed, containing markers equally spaced from one another at a distance of 15 µm. The markers that co-localize with TOMA immunoreactivity are labeled as positive, whereas the remaining markers are labeled negative. The area fraction is calculated as the number of positive markers divided by the total number of markers. The stereological assessment is made in a blinded fashion. The statistical analysis for the area fraction of TOMA immunoreactivity is performed using one-way ANOVA, followed by Bonferroni's multiple comparison test to allow for comparisons between groups, All statistical analysis are performed using GraphPad Prism program.

Example 3

Biochemical Analysis of Tau Oligomers in Ad Brain

Detailed biochemical analysis of Tau oligomer burden in AD brain is not available, although recent studies reported elegant biochemical analysis of Tau oligomers in the mouse brain (Berger et al., 2007; Spires et al., 2006). Tau aggregates range between dimer and pre-filament; the biochemical analysis will complement immunohistochemical analysis and provides information about the molecular weight of a specific oligomeric species associated with AD progression. Also, previous work on Aβ oligomers revealed the presence of more than one type of oligomeric species (Glabe, 2008); the proposed biochemical analysis will help in identifying different types of Tau oligomers in AD brain and their biochemical properties.

Western Blot and Dot Blot Analysis of Human Brain Tissue.

To determine if the progression of disease can be observed with TOMA, a large population of brains from patients with a broad range with respect to Mini Mental Status and Braak & Braak changes for the presence of Tau oligomers are analyzed. Frozen tissue from AD, MCI and age matched controls are tested. The regions of interest examined include entorhinal cortex, hippocampus, parietal lobe, olfactory bulb and frontal cortex. Tau oligomers are SDS stable. The PBS fraction, Triton X-100 fraction, and the Triton insoluble fraction are analyzed by western using TOMA, Tau-5, Tau-13, T46, pThr231, and pSer396.

Tissue Preparation and Initial Basic Analysis.

This procedure is based on experience in isolating different amyloid species from brain samples. The following fractions are analyzed by western and dot blot using TOMA, AT8, Tau-5 and other antibodies as required: the PBS soluble fraction, the Triton X-100 soluble fraction, and the Triton X-100 insoluble fraction. In addition, urea and formic acid denaturing treatments of the Triton insoluble fraction is performed and compared to the signal from the untreated control; this will allow quantification of any large Tau oligomers might have precipitated during the fractionation protocol.

Formic Acid and Urea Treatment:

Urea treatment; Both PBS soluble and Triton soluble human brain fractions are treated with, 0.375 M, 0.75 M, 1.5 M, 3 M, 6 M and 8M Urea. Samples are incubated overnight at room temperature before being analyzed.

Formic Acid Treatment:

PBS soluble human brain fraction is treated with 88%, 40%, 20% and 10% formic acid, mixed and incubated overnight at room temperature. Samples are analyzed by western blot using TOMA, AT8 and tau-5. In some cases additional antibodies are used.

Detergent Treatment.

Both PBS soluble and Triton soluble human brain fractions with 2%, 1%, 0.5%, 0.25%, 0.125%, 0.0625%, 0.03125%, and 0.015625% solutions of the detergents SDS, OG, OTG, CHAPS, Triton X100, Nonidet P-40, Tween 20, and BRIJ 58 are used. Samples are mixed and incubated overnight at +4° C., with the exception of SDS due to its propensity to precipitate at +4° C. SDS samples are incubated overnight at room temperature. These samples are analyzed by the dot blot assay using TOMA, AT8 and Tau-5.

Proteinase K, DNAse and RNAse Treatment.

Both PBS soluble and Triton soluble human brain fractions are treated with treated with different concentration of Proteinase K, DNAse and RNAse and incubated for one hour at 37° C., then analyzed by western blot using TOMA, AT8 and tau-5 antibodies. In all of the experiments in vitro prepared Tau oligomers and untreated samples are used as controls.

Quantitation of Tau Oligomers and Statistical Analysis:

In evaluating the correlation between TOMA signal and various parameters (Braak and Braak stage, post mortem index (PMI), gender, age at death and Mini-Mental State Examination (MMSE) score, the blots will be scanned and signal quantitated using Scion Imaging Software. The R2 value is calculated for TOMA signal from each fraction and correlated with MMSE score. Of greater interest, however, is the correlations between Tau oligomers in the PBS soluble and Triton soluble fractions and MMSE score. Data is statistically analyzed via ANOVA and unpaired two-tailed t-test with the GraphPad Prism program (ISI, Philadelphia, Pa.). $P<0.05$ is considered statistically significant.

Example 4

Tau Oligomers in CSF Samples

A Simple, non-invasive test for early detection of AD is highly needed. Tau or one of its many species (t-Tau and p-tau, p-tau-181 etc.) is part of all published CSF biomarker signatures for early detection of AD. It is well established that Tau levels are increased in the CSF, while Aβ levels are decreased in CSF from AD patients. The levels of Tau oligomers in CSF have not been evaluated, and data demonstrate that measuring the levels of Tau oligomers in the CSF by TOMA can be a biomarker for AD. Keep in mind that CSF is in direct contact with the CNS; therefore changes in its biochemical composition, such as an increase in Tau oligomers levels, would be evident in the CSF. Further, CSF is accessible in living patients through lumbar puncture.

CSF Samples.

Frozen CSF samples were obtained from the Institute for Brain Aging and Dementia (UC Irvine), Prof. John Ringman (Mary S. Easton Center for Alzheimer's Disease Research, UCLA), Prof. Martin Ingelsson (Uppsala University) and Prof. Douglas Galasko (Shiley-Marcos Alzheimer's Disease Research Center, UCSD). MMSE scores are available for all patients. CASI scores available for the presymptomatic patients (UCLA).

Quantification of Tau Oligomers in CSF Samples by Direct ELISA:

A standard ELISA protocol is used: 20-50 µl of CSF (16-40 µg total protein) is used in triplicate for each experiment and is measured in at least two independent experiments, TOMA, Tau-5, HT7 and pThr181 are used.

Quantification of Tau Oligomers in CSF Samples by IP/Western:

Standard protocols are used, both TOMA and Tau-5 are used to coat beads. For IP, 0.5-1 ml CSF is used in each experiment. The samples are probed on western using TOMA, T2286, Tau-5, HT7 and pThr181.

Quantification of Tau Oligomers in CSF by Sandwich ELISA:

Solid phase sandwich ELISA is used to detect tau oligomers in CSF. The inventors use Tau-5 antibody to capture all tau species present in the CSF. 20 µl of CSF is used in each experiment. HT7 and pThr181 are also used as "capture" antibodies. TOMA and pThr181 are used as the detection antibody.

Data Analysis:

Statistical analysis is performed on the ELISA and sandwich ELISA data. Data is statistically analyzed via ANOVA and unpaired two-tailed t-test with the GraphPad Prism program. The differences are considered statistically significant if the p-value≤0.02. Immunoprecipitation (IP)/western data is analyzed by scanning the blots and quantitating the signal using. The R2 value is calculated and correlated with MMSE score. All data shared with the samples provides to further analyze the data and its significance based on the clinical and neuropathological characterization of the patients other than the MMSE.

Example 5

Tau Oligomers in Mouse Models

Mouse models of AD are used to investigate the role of tau oligomers in mediating Aβ toxicity and AD related phenotypes, Tg2576 is one example of such a model; Tg2576 is well-characterized and has been used in numerous studies with great reproducibility. Moreover, it has the same Swedish mutation as the hAPP-J20 mouse model used to discover the role of tau in Aβ mediated toxicity. The Tg2576 mouse has secondary tauopathy, and the presence of phosphorylated tau species in the brain of these animals has been reported. Moreover, data demonstrate the presence of tau oligomers in this model. The APP/PS1 model is a more aggressive model, amyloid deposits start at 8 weeks—by 4.5 months, it shows deposition of phosphorylated tau, and at 16 months it shows tau PHF-like structures. Tau oligomers in this model show at 6 months old.

Selection of Mouse Models of Tauopathy:

The dissociation between NFT formation and phenotypes observed in mouse models of tauopathy indicates that oligomeric assemblies of tau are the most toxic tau species formed. This phenomenon is universal for all tauopathy models, meaning that one can choose any tau model to analyze using TOMA. The inventors analyze brains from the h-tau mice, as this model shows extensive cell death and synaptic lesions independently of NFT formation, as well as the P301L (JNPL3), the latter model was used in the sole published tau active vaccination study and data show abundant tau oligomers at an early age confirmed by IHC, Western, and thus it is the logical choice for passive vaccination study using TOMA. By choosing two well-established models the inventors are able to evaluate the formation of tau oligomers and confirm their role as mediator for Aβ toxicity.

IHC and Biochemical Analysis of Tau Oligomers in Mouse Models:

Mouse brains are analyzed using the same methods described for the human brain samples. These methods include IHC in paraffin sections, frozen sections, Western blot, and ELISA, primarily using TOMA; in combination with Tau 5, Tau 13, pThr231, p422, AT100, and AT8. The initial analysis includes the following ages for each mouse model; most of these brain samples are extracted from animal colonies, whereas others like the h-tau are provided by collaborators, Dr. K. Duff and others. These time points are selected based on the published literature describing these animals' phenotypes:

Tg2576 Model:
Brains are analyzed at 5, 6, 8, 9, 10, 12 and 16 months.
App/Psi Model:
Brains are analyzed at 3, 6, 8, and 10 months.
h-Tau Model:
Brains are analyzed from 5, 7, 8, 10 and 16 month old mice.
P301L Model:
Brains are analyzed at 2½, 3, 4, 5, 6, 7, 8, and 10 months.
Data Analysis:

ELISA measurements are analyzed using ANOVA and unpaired two-tailed t-test with the GraphPad Prism program. The differences are considered statistically significant if the p-value≤0.05. Western and dot blot data is analyzed by scanning the blots and quantitating the signal using Scion Imaging Software. The R2 value is calculated and correlated with age.

P301L (JNPL3) mouse model is vaccinated because it was the model used in the published tau immunotherapy; results will be directly comparable from TOMA passive vaccination with the results of Asuni et al. using active vaccination targeting phosphorylated tau and NFT.

As an AD model the Tg2576 mouse is vaccinated that expresses the Swedish mutation of hAPP: (1) This model is well-characterized and has been used in numerous passive vaccination studies targeting Aβ, enabling cross comparison, (2) This mouse model was used to develop the hAPP-J20 mouse model (7), and finally, the inventors are able to detect tau oligomers using TOMA in this model.

Both intracerebroventricular (i.c.v) and intraperitoneal (i.p.) injections are contemplated to deliver TOMA, the inventors chose to start with i.c.v. as described in well-executed studies that investigated the delivery of anti-Aβ antibodies into the Tg2576 mouse model and other AD models. These studies demonstrated that i.c.v. injection is effective and minimize the side effects associated with amyloid clearance when compared side by side with i.p. injections, which also require higher doses of antibody. In addition, i.c.v. delivered TOMA engage only central mechanisms for clearing tau oligomers and do not require involvement of the peripheral mechanisms proposed to be involved in the clearance of Aβ.

Passive Vaccination of the Tauopathy Model P301L Using TOMA.

The P301L model develops minor sensory-motor abnormalities by 3 months and NFT at 4 months old. Groups of mice ages 3, 4, 6, 7, and 9 months are vaccinated by a single bolus i.c.v injection of 2 µg of TOMA in the left hemisphere; control mice are i.c.v. injected with PBS or control IgG. Behavioral analyses are performed 3 days prior to the injection and 4 days after the injection. These tests include Rotarod, and Traverse beam and Object recognition. Animals are terminated 1 week after the injection; brains are extracted and dissected for ICH and biochemical analyses. A longer time between injection and the termination of the animal is also contemplated; this will help in understanding the dynamics between tau oligomers and other tau aggregates. The IHC analyses from these brains are used to evaluate the relationship between extracellular and intracellular tau oligomers. The behavioral abnormalities in the P301L mouse model are evaluated by performing the following tests, Rotarod, Traverse Beam, and Object recognition.

Passive Vaccination of the AD Model Tg2576 Using TOMA.

The Tg2576 model shows memory decline starting at 6 months, whereas Aβ amyloid plaques start to deposit at 9 months. These animals show severe memory deficits between 6-12 months old; Aβ oligomers at 6 months, long before plaque formation, groups of mice ages 6, 8, 10, and 12 months are vaccinated by i.c.v injection of 2 µg TOMA in the left hemisphere; control mice are i.c.v. injected with PBS or control IgG. Behavioral and memory tests are performed 4 days prior to the injection and 4 days after the injection; these tests include fear-conditioning and locomotor activity. Animals are terminated 1 week after the injection; brains are extracted and dissected for IHC and biochemical analysis. Behavioral and memory tests are performed and include, Fear Conditioning, Morris Water Maze, and Locomotor activity.

Data Analysis:

Tau oligomer levels in the brains of these animals are analyzed as described herein. First, both total tau and tau oligomers levels from these animals before vaccination is quantified by TOMA for tau oligomers and Tau 5 and Tau 13 for total tau. Then tau oligomer and total tau levels before and after the passive vaccination are calculated and compared. Finally, tau oligomer levels are correlated with the results of the behavioral tests. The data from the rotarod, fear conditioning and traverse beam is analyzed by two-way ANOVA repeated measures and a Bonferroni post hoc test using the. Data from the locomotor activity measurements, Morris water maze and object recognition test are analyzed using the unpaired two-tailed t-test. Correlation between behavioral outcome and tau oligomers levels are evaluated and analyzed by Pearson r correlation. The R2 values are calculated.

Example 6

Animal Model of Traumatic Brain Injury

Rat Model.

Male Sprague-Dawley rats (Charles River Laboratories, Wilmington, Mass.) (400-500 g) were anesthetized with 4% isoflurane, intubated, mechanically ventilated with 1.5% isoflurane in $O_2$:air (20:80) using a volume ventilator (NEMI Scientific, Medway, Mass., USA), and prepared for moderate or sham parasagittal fluid percussion injury as described previously in Hawkins et al., (2012) and Li et al., (2010). Rectal and temporalis muscle temperatures were monitored using telethermometers (Physitemp Instruments Inc., Clifton, N.J., USA), and temperatures were maintained within a range of 37.5+/−0.5° C. using an overhead lamp and a thermostatically controlled water blanket (Gaymar Industries Inc., Orchard Park, N.Y., USA). Rats were placed in a stereotaxic apparatus, a midline incision of the skin was performed, and the skull was exposed. With the use of a Michele trephine, a craniotomy was performed 1 mm lateral (right) to the sagittal suture, midway between the lambda and bregma. The bone chip was removed, leaving the dura intact. A modified 20-gauge needle hub was secured in place over the exposed dura with cyanoacrylic adhesive and cemented into place with hygienic dental acrylic.

Parasagittal Fluid Percussion Injury.

TBI was administered by means of a fluid percussion injury device (Dixon et al., 1987) consisting of a fluid-filled Plexiglas cylinder 60-cm-long and 4.5 cm in diameter, one end of which was connected to a hollow metal cylinder housing a pressure transducer (Statham PA856-100, Data Instruments Inc., Acton, Mass., USA), with the other end closed by a Plexiglas piston mounted on O rings. The transducer housing was connected to the rat by a plenum tube at the craniotomy site. Each TBI was induced by dropping a 4.8 kg steel pendulum that struck the piston. The height of the pendulum determined the intensity of the injury. The fluid pressure pulse was recorded on an oscilloscope triggered photoelectrically by the descent of the pendulum. At 4 hr and at 24 hr after TBI or sham injury (n=6 at each time point), rats were re-anesthetized and transcardially perfused with chilled saline to remove blood, and then brains were collected and immediately frozen.

Example 7

Identification and Analysis of Tau Oligomers in Rat Brains Following TBI

Whether Tau oligomers form in non-transgenic animals in response to TBI was unknown. The presence of Tau oligomers in rat brains was determined at 4 hr and 24 hr following traumatic brain injury.

ELISA.

For ELISA, plates were coated with 10 μl of the brain extract using 0.1 M sodium bicarbonate, pH 9.6, as coating buffer, followed by an overnight incubation at 4° C., washed three times with Tris-buffered saline with Tween (0.01%) (TBST), then blocked for 3 hr at room temperature with 10% nonfat dry milk in TBST. The plates were then washed with TBST. Antibodies for use in ELISA included anti-Tau oligomer antibody T2286 (1:500), Anti-Tau-1 (1:1000) (clone PC1C6/MAB3420; EMD Millipore; Billerica, Mass., USA), Anti-GAPDH (1:1000) (Abcam, Cambridge, Mass., USA), AT8 (1:1000) (anti-Phospho-PHF-tau pSer202/Thr205, Clone AT8; Thermo Scientific, Waltham, Mass., USA), and AT180 (1:1000) (anti-Phospho-PHF-tau pThr231, Clone: AT180; Thermo Scientific, Waltham, Mass., USA). All antibodies were diluted in 5% nonfat milk in TBST and were added and allowed to react with antigen for 1 hr at room temperature. ELISA plates were then washed three times with TBST, 100 μl of horseradish peroxidase-conjugated anti-rabbit IgG (1:3000; GE Healthcare Life Sciences, Piscataway, N.J., USA) was added, and plates were incubated for 1 hr at room temperature. Finally, plates were washed three times with TBST and developed with 3,3',5,5',-tetramethylbenzidine (TMB-1 component substrate) (DAKO; Carpinteria, Calif., USA). Color development was stopped with 100 μl of 1 M HCl, and absorbance was measured at 450 nm using a POLARstar OMEGA plate reader (BMG LABTECH, Ortenberg, Germany).

Figures 11A, 11B, 11C, 11D:
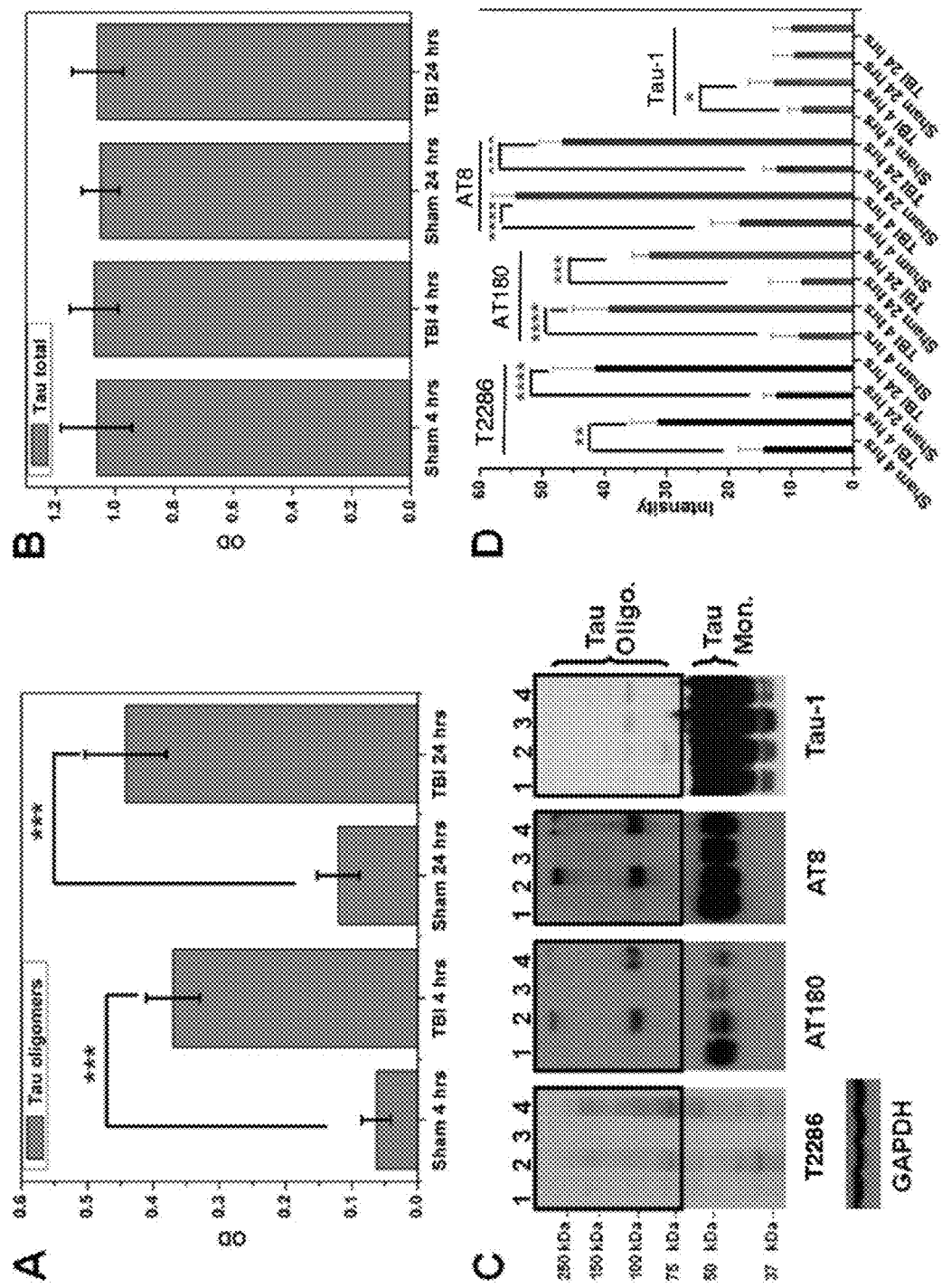
FIGS. 11A-11D. Tau oligomer accumulation after TBI. (A-B) ELISA analysis of (A) Tau oligomers and (B) total Tau protein, in brain extracts from sham-TBI and TBI rats at 4 hr and 24 hr post TBI. (C) Western blot of extracts from (1) sham brain after 4 hr, (2) TBI brain after 4 hr, (3) sham brain after 24 hr, and (4) TBI brain after 24 hr probed with T2286, AT180, ATB, Anti-Tau-1 antibodies, and anti-GAPDH (loading control) antibodies. Boxed regions of blots represent bands of oligomeric Tau species (Tau oligo.). Tau Mon., Tau monomers. (D) Quantification of oligomeric Tau species present in the boxed regions of the blot in FIG. 11C (n=6); **, $p<0.0001$; *, $p<0.0005$; **, $p<0.001$; *, $p<0.05$.

At 4 hr and 24 hr after moderate parasagittal fluid percussion injury, Tau oligomers were observed by ELISA, using anti-Tau oligomer antibody T2286, to be significantly increased in TBI brain extracts when compared with sham brain extracts (p<0.001 TBI versus sham) (FIG. 11A). However, using the Anti-Tau-1 antibody, no difference in total Tau protein was observed between extracts from TBI and sham brains at 4 hr and at 24 hr (FIG. 11B). High levels of total Tau protein were observed in all samples. These results were indicative of Tau oligomerization, rather than overproduction of Tau, following TBI.

Western Blots and Analysis.

Tissue samples were homogenized in 5% ice-cold protease inhibitor. Brain extracts (16 μl) were mixed with 4 μl of 4× sample buffer (without boiling), separated on 4-12% Bis-Tris SDS-PAGE gels, and subsequently transferred onto nitrocellulose membranes. After blocking overnight at 4° C. with 10% nonfat milk, membranes were incubated for 1 hr at room temperature with T2286 (1:200), Anti-Tau-1 (1:1000), Anti-GAPDH (1:1000), AT8 (1:1000), or AT180 (1:1000) diluted in 5% nonfat dried milk. For detection, horseradish peroxidase-conjugated anti-rabbit IgG and anti-mouse IgG (1:3000; GE Healthcare) and ECL plus (GE Healthcare) were used. Western blot densitometry analysis was performed using LabWorks Software version 4.5 (UVP, LLC, Upland, Calif., USA). For protein quantification, the density of each band in the Western blot was normalized with GAPDH. All densitometry results represented the mean and standard deviation (S.D.) (n=6).

Western blot analyses with various antibodies were used to determine the conformation and aggregation state of Tau proteins following TBI (FIG. 11C). The results were similar to those observed with ELISA and confirmed that Tau oligomers, observed as high molecular weight bands in FIG. 11C boxed area (Tau Oligo), were significantly increased at both 4 hr and 24 hr after TBI (FIG. 11D). No significant differences in the quantities of total Tau detected with Anti-Tau-1 (Tau-1) were observed between sham and TBI at 4 hr or at 24 hr after TBI (FIG. 11D). Because hyperphosphorylation of Tau plays a major role in NFT formation (Augustinack et al., 2002), two different antibodies (AT8, AT180) were used to examine the presence of phosphorylated Tau in the samples (FIG. 11C). Western blots using AT8, which detects Tau phosphorylation at Ser202 and Thr205, and AT180, which detects Tau phosphorylation at Thr231, revealed the increased presence of phosphorylated Tau dimers and large aggregates (Tau Oligo) in TBI samples as compared to sham samples, confirming the significant increase in SDS-stable phosphorylated Tau oligomers after TBI (FIG. 11C, FIG. 11D). Non-phosphorylated monomeric Tau levels (Tau Mon.), detected with Anti-Tau-1 (Tau-1), were unchanged in TBI compared with sham brains (FIG. 11C, FIG. 11D). All blots were normalized to GAPDH protein.

Statistical Analyses.

Data were analyzed by one-way analysis of variance followed by Bonferroni's correction for multiple comparisons using GraphPad Prism software (version 5) (GraphPad Software, San Diego, Calif., USA) and OriginPro software version 8.0 (OriginLab Corp., Northampton, Mass., USA). Data in the text and figures are represented as the mean+/−S.D.

Example 8

Isolation of Tau Oligomers from Rat Brains Following TBI

To further characterize Tau oligomers formed after TBI, Tau oligomers were isolated from rat brains 24 hr post-TBI by immunoprecipitation and analyzed by size-exclusion chromatography and atomic force microscopy.

Isolation and Characterization of Tau Oligomers-Derived Tau Species from TBI or Sham Injury Brain Homogenates.

Isolation of Tau oligomer by immunoprecipitation was performed as described previously, (Lasagna-Reeves et al., 2011; Lasagna-Reeves et al., 2012). Briefly, tosyl-activated magnetic Dynabeads (Dynal Biotech, Lafayette Hill, Pa., USA) were coated by incubating overnight at 37° C. with 20 μg of anti-Tau oligomer antibody T2286 (1.0 mg/ml) diluted in 0.1 M borate, pH 9.5. Beads were washed with 0.2 M Tris (pH 8.5) containing 0.1% bovine serum albumin, then incubated with either the 24 hr TBI or sham brain homogenate with rotation at room temperature for 1 hr. Beads were then washed three times with PBS and eluted using 0.1 M glycine, pH 2.8. The pH of each eluted fraction was adjusted using 1 M Tris, pH 8.0. Fractions were pooled and concentrated 5-fold using Amicon® Ultra Centrifugal Filter units with 30-kDa cut-off (EMD Millipore Corp., Billerica, Mass., USA). Characterization of Tau oligomers isolated by immunoprecipitation was performed as described previously (Lasagna-Reeves et al., 2010; Lasagna-Reeves et al., 2012). Size-exclusion chromatography analysis was performed using an LC-6AD HPLC system (Shimadzu Scientific Instruments, Columbia, Md., USA) fitted with a Superdex 200-10/300 GL column (GE Healthcare). For column injection, isolated Tau oligomer sample (6 µl) was adjusted to 50 µl of total volume with filtered 1×PBS. Running buffer (1×PBS) was used with a flow rate of 0.8 ml/min. The approximate molecular weight of the peaks was estimated using gel filtration standard (Bio-Rad Laboratories, Inc., Hercules, Calif., USA) (Lasagna-Reeves et al., 2010; Lasagna-Reeves et al., 2012). The morphology of Tau oligomers isolated by immunoprecipitation was assessed as previously described (Lasagna-Reeves et al., 2010; Lasagna-Reeves et al., 2012) by atomic force microscopy (AFM) using a non-contact tapping method (ScanAsyst-Air) with a Multi-Mode® 8 AFM machine (Bruker Corp., Santa Barbara, Calif., USA).

Figures 12A, 12B, 12C:
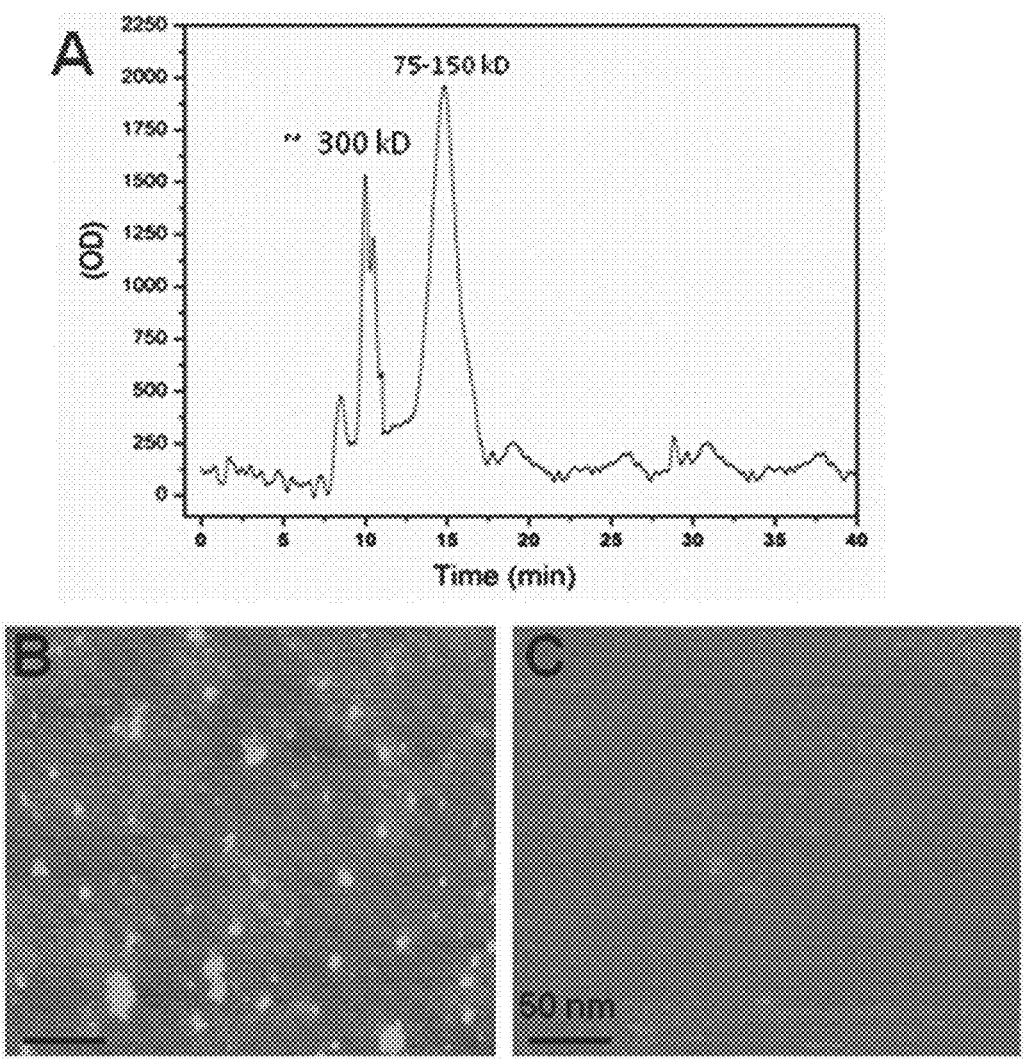
FIGS. 12A-12C. Isolation and characterization of Tau oligomers from TBI brains. Tau oligomers were isolated by immunoprecipitation from rat brain extracts 24 hr after TBI, using anti-Tau oligomer antibody T2286. (A) Size exclusion chromatogram of Tau oligomers showing two main peaks, one at 75-150 kDa, which may include Tau dimers and trimers, and a second at ~300 kDa. (B) AFM image of TBI brain-derived Tau oligomers. (C) AFM image of the material isolated from sham brains.

A size exclusion chromatogram (FIG. 12A) showed that the isolated oligomers are heterogeneous, with two major peaks, one at approximately 100 kDa-150 kDa and a second at approximately 300 kDa. AFM images confirmed the heterogeneous nature of the oligomers derived from TBI brains, but despite this, no fibrillar material was detected in the isolated oligomers (FIG. 12B). Moreover, no oligomers were found in the immunoprecipitation samples from sham rat brains (FIG. 12C).

Example 9

Immunofluorescence Analysis of Tau Oligomers in Brains from Rats Following TBI

Tau oligomers-derived Tau species occurring in brain sections from rats following TBI were characterized by immunohistochemistry.

Immunofluorescence.

Frozen sections were fixed with chilled acetone for 10 min at room temperature. After blocking in normal goat serum for 1 hr, sections were incubated overnight with anti-Tau oligomer antibody T2286 (1:300). The following day, sections were washed three times for 10 min each in PBS and incubated for 1 hr with goat anti-rabbit IgG Alexa Fluor 568 diluted at 1:350 (Invitrogen, Life Technologies Corp., Carlsbad, Calif., USA). The sections were then washed three times for 10 min each in PBS before incubation overnight with Anti-Tau-1 diluted at 1:200 (EMD Millipore). The following day, sections were washed in PBS three times for 10 min each prior to incubation for 1 hr with goat anti-mouse IgG Alexa Fluor 488 diluted 1:350 (Invitrogen). The sections were then washed three times for 10 min each with PBS. Sections were incubated with DAPI diluted 1:3000 in PBS for 5 min, washed, and mounted in Fluoromount-G mounting medium (Southern Biotech, Birmingham, Ala., USA). The sections were examined using a Bio-Rad Radiance 2100 confocal system mounted on a Nikon Eclipse E800 microscope equipped with a CoolSnap-FX monochrome CCD camera (Photometrics, Tucson, Ariz., USA) using standard Nikon FITC, Texas Red, and DAPI filters set for Alexa Fluor 488 and 568, and DAPI, respectively.

Peroxidase Immunohistochemistry.

Peroxidase immunohistochemistry was performed on frozen sections. Sections (5 µm) were fixed with chilled acetone for 10 min at room temperature and blocked for 1 hr with 5% horse serum in PBS. Antibodies for use in immunohistochemistry included anti-Tau oligomer antibody T2286 (1:300), AT8 (1:100), and AT180 (1:100). Primary antibodies were incubated overnight at 4° C. and detected with biotinylated goat anti-mouse IgG (Vectastin ABC kit; Vector Laboratories, Burlingame, Calif., USA) or biotinylated goat anti-rabbit IgG (Vectastin ABC kit; Vector Laboratories) and visualized using a 3,3'-diaminobenzidine peroxidase substrate kit (Vector Laboratories) according to the manufacturer's instructions. Sections were counterstained with hematoxylin (Vector Laboratories) for nuclear staining. Brightfield images were acquired using a Nikon Eclipse 800 microscope equipped with a Nikon DXM1200 color CCD camera (Nikon Instruments, Inc., Melville, N.Y., USA).

At 24 hrs after TBI, total Tau protein and Tau oligomers were detected by immunofluorescence in the hippocampus (HC) and cortex of rats. Tau protein was detected in the hippocampus and cortex of rats from the sham groups. However, Tau oligomers were not detected in the hippocampus or cortex of sham rats. Merged images, which also included a DAPI stain, revealed that the oligomer seeds detected by anti-Tau oligomer antibody T2286 are formed from Tau aggregations and represent a small fraction of total Tau protein, consistent with the results obtained by Western blot analyses shown in FIG. 11C.

Using peroxidase immunohistochemistry and AT180, phosphorylated Tau was detected in the CA3 region of the hippocampus, the dentate gyms, and the cortex, in sections from brains at 24 hr after TBI. The presence of Tau oligomers in the cortex and hippocampus was confirmed by peroxidase immunohistochemistry with T2286. Tau oligomers were observed in the CA3 region and the dentate gyms of the hippocampus in sections from brains at 24 hr after TBI.

In other peroxidase immunohistochemistry experiments, Tau oligomers were detected with T2286 and phosphorylated Tau was detected with AT8, in both the cortex and hippocampus brain regions at 2 weeks after TBI. Peroxidase immunohistochemistry revealed Tau oligomers in contralateral and ipsilateral regions of the cortex, the hippocampus, the dentate gyms of the hippocampus, and the CA1/2 regions of the hippocampus at 2 weeks post TBI. Oligomeric Tau was not detected in sham control brains. Phosphorylated Tau (AT8) was present at 2 weeks post TBI, ipsilaterally in the cortex, the hippocampus, the dentate gyms of the hippocampus, and the CA1/2 regions of the hippocampus regions of rat brains. Sham brains were used as a control and displayed significantly less AT8 staining.

Figure 13:
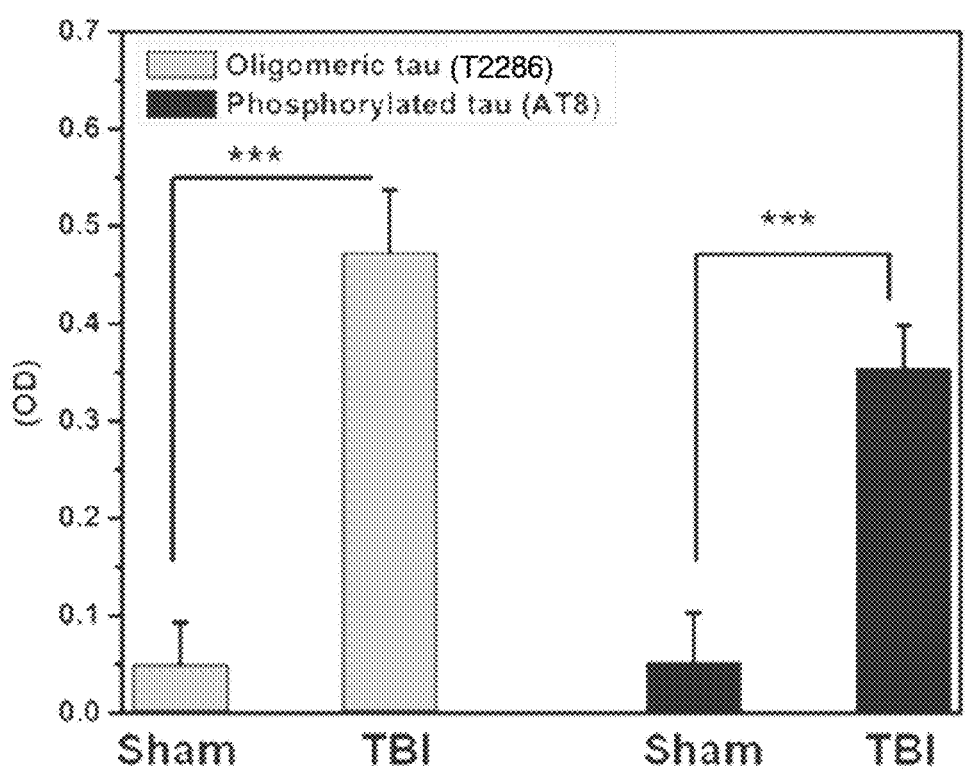
FIG. 13. Detection of Tau oligomers 2 weeks after TBI. ELISA analysis of Oligomeric Tau (T2286, left side, lighter bars) and phosphorylated Tau protein (AT8, right side, darker bars) in brain extracts from TBI rats (TBI) and sham-TBI rats (Sham) at 2 weeks post TBI. Samples (n=2) were measured in triplicate. ***, $p<0.0005$.
Figure 14:
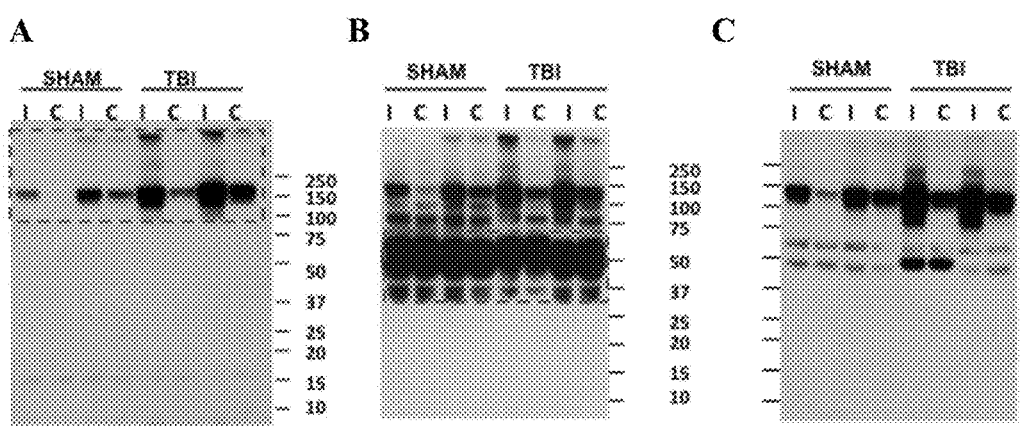
FIG. 14. Western blot from TBI mice brain homogenates with H12 & Tau 5 antibodies. (A) Detection of Tau oligomers using Tau oligomer monoclonal antibody (TOMA) clone H12. (B) Detection of total Tau using Tau5 antibody. (C) Detection of phosphor-Tau using AT180 antibody. Homogenates are from ipsilateral (I) and contralateral (C) regions of TBI or Sham brain cortices.
Figure 15:
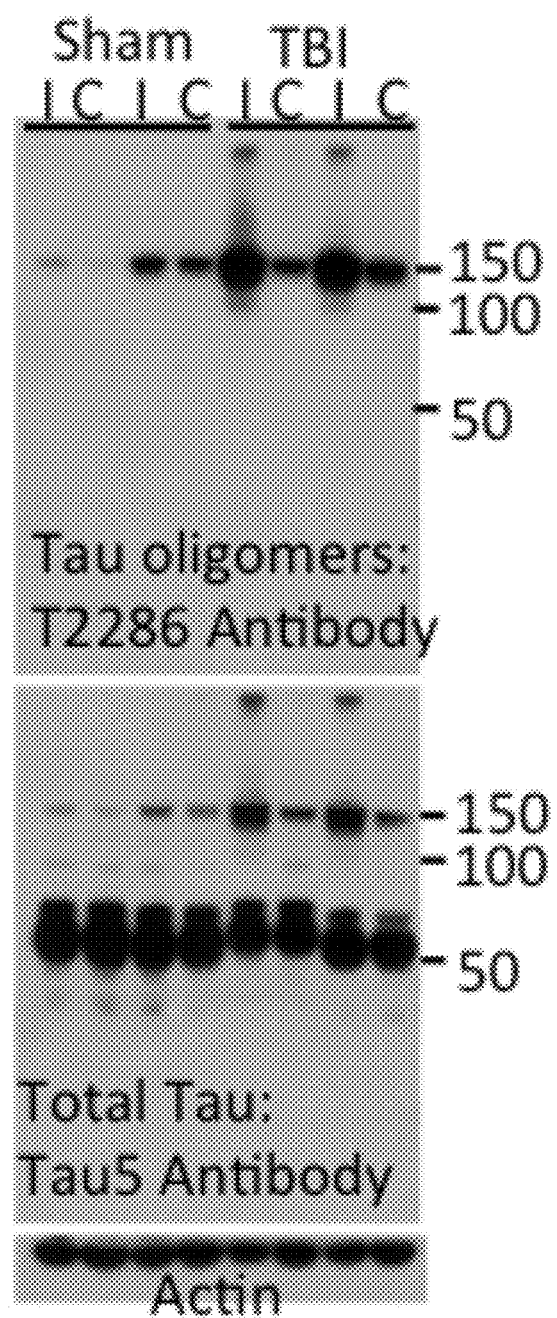
FIG. 15. Tau oligomers increase after TBI in 3×Tg-AD mice: Western blotting of ipsilateral (I) and contralateral (C) hippocampal TBS-lysates prepared 24 hours after controlled cortical impact injury (TBI) or sham (no injury) in 6 month old 3×Tg-AD mice. Ipsilateral to injury there is a shift to higher molecular weight tau species, immunoreactive with T22.

The TBI model used here induces cellular damage to the injured (ipsilateral) side of the brain and oftentimes causes nonlethal cellular changes to the uninjured (contralateral) hemisphere (Rojo et al., 2011). This was confirmed by direct ELISA using T2286 and AT8 (FIG. 13). Statistically significant differences were observed in the levels of Tau oligomers (T2286, left side, lighter bars) and phosphorylated Tau (AT8, right sight, darker bars) in brain extracts from rats at 2 weeks post-TBI (TBI) and post-sham-TBI rats (Sham).

REFERENCES

The following references, to the extent that they provide exemplary procedural or other details supplementary to those set forth herein, are specifically incorporated herein by reference.

U.S. Pat. No. 4,338,298
U.S. Pat. No. 4,554,101
U.S. Pat. No. 4,748,018
U.S. Pat. No. 5,512,282
U.S. Pat. No. 5,548,066
U.S. Pat. No. 6,651,655
U.S. Pat. No. 6,756,361
U.S. Pat. No. 6,770,278
U.S. Pat. No. 6,936,258
Alafuzoff et al., *Brain Pathol.*, 18(4):484-96, 2008.
Alonso et al., *Curr. Alzheimer Res.*, 5(4):375-84, 2008.
Alonso et al., *Proc. Natl. Acad. Sci. USA*, 98(12):6923-8, 2001a.
Alonso et al., *J. Biol. Chem.*, 276(41):37967-73, 2001b.
Andorfer et al., *J. Neurosci.*, 25(22):5446-54, 2005.
Andreasen et al., *Neurosci. Lett.*, 273(1):5-8, 1999.
Arriagada et al., *Neurology*, 42(3 Pt 1):631-9, 1992.
Ashe, *N. Engl. J. Med.*, 357(9):933-5, 2007.
Asuni et al., *J. Neurosci.*, 27(34):9115-29, 2007.
Augustinack et al., *Acta Neuropathol.*, 103(1):26-35, 2002.
Avila et al., *Curr. Alzheimer Res.*, 1(2):97-101, 2004.
Avila, *FEBS Lett.*, 476(1-2):89-92, 2000.
Avila, *J. Cell Mol. Med.*, 12(1):258-9, 2008.
Ballatore et al., *Nat. Rev. Neurosci.*, 8(9):663-72, 2007.
Barany and Merrifield, In: *The Peptides*, Gross and Meienhofer (Eds.), Academic Press, NY, 1-284, 1979.
Baumann et al., *FEBS Lett.*, 336(3):417-24, 1993.
Berger et al., *J. Neurosci.*, 27(14):3650-62, 2007. Biernat et al., *Neuron.*, 11(1):153-63, 1993.
Binder et al., *J. Cell Biol.*, 101(4):1371-8, 1985. Bird et al., *Brain.*, 122 (Pt 4):741-56, 1999.
Blom et al., *Dement. Geriatr. Cogn. Disord.*, 27(5):458-64, 2009.
Bondareff et al., *J. Neuropath. Exper. Neurol.*, 53(2):158-164, 1994.
Borroni et al., *Eur. J. Pharmacol.*, 545(1):73-80, 2006.
Braak and Braak, *Acta Neuropathol.*, 82(4):239-59, 1991a.
Braak and Braak, *Brain Pathol.*, 1(3):213-6, 1991b.
Braak and Braak, *Acta Neurol. Scand. Suppl.*, 165:3-12, 1996.
Bretteville and Planel, *J. Alzheimers Dis.*, 14(4):431-6, 2008.
Brunden et al., *J. Alzheimers Dis.*, 14(4):393-9, 2008.
Buee et al., *Brain Res. Brain Res. Rev.*, 33(1):95-130, 2000.
Buerger et al., *Brain*, 129(Pt 11):3035-41, 2006.
Bulic et al., *Angew Chem. Mt. Ed. Engl.*, 48(10):1740-52, 2009.
Burke et al., *J. Inf. Dis.*, 170:1110-1119, 1994.
Busciglio et al., *Neuron.*, 14(4):879-88, 1995.
Cash et al., *Am. J. Pathol.*, 162(5):1623-7, 2003.
Clark et al., *Proc. Natl. Acad. Sci. USA*, 95(22):13103-7, 1998.
Congdon and Duff, *J. Alzheimers Dis.*, 14(4):453-7, 2008.
De Felice et al., *Neurobiol. Aging*, 29(9):1334-47, 2008.
Delacourte and Buee, *Curr. Opin. Neurol.*, 13(4):371-6, 2000.
Demuro et al., *J. Biol. Chem.*, 280(17):17294-300, 2005.
Dixon et al., *J. Neurosurg.*, 67:110-119, 1987.
Drechsel et al., *Mol. Biol. Cell*, 3(10):1141-54, 1992.
Drewes et al., *EMBO J.*, 11(6):2131-8, 1992.
Drewes et al., *J. Biol. Chem.*, 270(13):7679-88, 1995.
Epitope Mapping Protocols, 1996.
Ferrari et al., *Biochem. Biophys. Res. Commun.*, 337(4):1097-101, 2003.
Folstein et al., *J. Psychiatr. Res.*, 12(3):189-98, 1975.
Galasko et al., *Neurology*, 48(3):632-5, 1997.
Glabe, *J. Biol. Chem.*, 283(44):29639-43, 2008.
Goedert et al., *Neuron.*, 8(1):159-68, 1992.
Goedert et al., *J. Neurochem.*, 65(6):2804-7, 1995.
Goedert et al., *EMBO J.*, 8:393-399, 1989.
Goedert et al., *Neuron.*, 3:519-526, 1989.
Gomez-Ramos et al., *FEBS Lett.*, 580(20):4842-50, 2006.
Gomez-Ramos et al., *Mol. Cell Neurosci.*, 37(4):673-81, 2008.
Gong and Iqbal, *Curr. Med. Chem.*, 15(23):2321-8, 2008.
Gotz et al., *Science*, 293(5534):1491-5, 2001.
Grundke-Iqbal et al., *Proc. Natl. Acad. Sci. USA*, 83(13):4913-7, 1986.
Haass and Selkoe, *Nat. Rev. Mol. Cell Biol.*, 8(2):101-12, 2007.
Hanger et al., *Neurosci. Lett.*, 147(1):58-62, 1992.
Hardy and Allsop, *Trends Pharmacol. Sci.*, 12(10):383-8, 1991.
Hardy and Selkoe, *Science*, 7(5580):353-6, 2002.
Harlow and Lane, In: *Antibodies: A Laboratory Manual*, Cold Spring Harbor Laboratory, Cold Spring Harbor, N.Y., 346-348, 1988.
Haroutunian et al., *Neurobiol. Aging*, 28(1):1-7, 2007.
Harper et al., *Chem. Biol.*, 4(2):119-25, 1997.
Hawkins et al., *Brain Res.*, 1432:28-35, 2012.
Hernandez and Avila, *J. Alzheimers Dis.*, 14(4):449-52, 2008.
Herukka et al., *Neurology*, 64(7):1294-7, 2005.
Honson et al., *Neurotox. Res.*, 15(3):274-83, 2009.
Huston et al., *Methods Enzymol.*, 203:46-88, 1991.
Hutton et al., *Nature*, 393(6686):702-5, 1998.
Iqbal and Grundke-Iqbal, *Drug News Perspect.*, 11(1):10-4, 1998.
Iqbal et al., *Acta Neuropathol.*, 118(1):53-69, 2009.
Jakes et al., *EMBO J.*, 10:2725-2729, 1991.
Johnson et al., *Biochem. Biophys. Res. Commun.*, 163(3):1505-11, 1989.
Johnson et al., *Arch Biochem Biophys.*, 291(2):371-8, 1991.
Johnson et al., *J. Cell Sci.*, 117(Pt 24):5721-9, 2004.
Karsten et al., *Neuron.*, 51(5):549-60, 2006.
Kayed and Glabe, *Methods Enzymol.*, 413:326-44, 2006.
Kayed et al., *Science*, 300(5618):486-9, 2003.
Kayed et al., *J. Biol. Chem.*, 279(45):46363-6, 2004.
Kayed et al., *Mol. Neurodegener.*, 2:18, 2007.
Kayed et al., *J. Biol. Chem.*, 284(7):4230-7, 2009.
Kohler and Milstein, *Nature*, 256:495-497, 1975.
Kostelny et al., *J. Immunol.*, 148:1547-1553, 1992.
Kurt et al., *Neurobiol. Dis.*, 14(1):89-97, 2003.
Kyte and Doolittle, *J. Mol. Biol.*, 157(1):105-132, 1982.
Lai et al., *Neurobiology of Ageing*, 16(3):433-445, 1995.
Larbig et al., *Curr. Alzheimer Res.*, 4(3):315-23, 2007.
Lasagna-Reeves et al., *Biochemistry*, 49:10039-10041, 2010.
Lasagna-Reeves et al., *J. Biol. Chem.*, 286: 22122-22130, 2011.
Lasagna-Reeves et al., *Faseb J.*, 26:1946-1959, 2012.
Lee et al., *Annu. Rev. Neurosci.*, 24:1121-59, 2001.
Li et al., *Brain Res.*, 1330:131-141, 2010.
Li et al., *Neurology*, 69(7):631-9, 2007.
Litersky et al., *J. Biol. Chem.*, 267(3):1563-8, 1992.
Litersky et al., *Brain Res.*, 604(1-2):32-40, 1993.
Maeda et al. *Neurosci. Res.*, 54(3):197-201, 2006.
Maeda et al., *Biochemistry*, 46(12):3856-61, 2007.

Margittai and Langen, *Proc. Natl. Acad. Sci. USA*, 101(28): 10278-83, 2004.
Margittai and Langen, *J. Biol. Chem.*, 281(49):37820-7, 2006.
Marx, *Science*, 316(5830):1416-7, 2007.
Matsuo et al., *Neuron.*, 13(4):989-1002, 1994.
Mayeux et al., *New Eng. J. Med.*, 341:1670-1679, 1999.
McKhann, *Neuropediatrics*, 15(Suppl):4-10, 1984.
Meier et al., *Am. J. Physiol. Endocrinol. Metab.*, 291(6): E1317-24, 2006.
Mena et al., *Acta Neuropathol.*, 89:50-56, 1995.
Mena et al., *Acta Neuropathol.*, 91:633-641, 1996.
Merrifield, *Science*, 232(4748):341-347, 1986.
Morishima-Kawashima et al., *Neurobiol. Aging*, 16(3):365-71, 1995.
Morsch et al., J. Neuropathol. Exp. Neurol., 58(2):188-97, 1999.
Motter et al., *Ann. Neurol.*, 38(4):643-8, 1995.
Novak et al., *EMBO J.*, 12:365-370, 1993.
Oddo et al., *J. Biol. Chem.*, 281(51):39413-23, 2006.
Parnetti et al., *Mech. Ageing Dev.*, 127(2):129-32, 2006.
Pennanen and Gotz, *Biochem. Biophys. Res. Commun.*, 337(4):1097-101, 2005.
Petersen et al., *Arch. Neurol.*, (3):303-8, 1999.
Pickhardt et al., *Curr. Alzheimer Res.*, 2(2):219-26, 2005.
Pittman et al., *Hum. Mol. Genet.*, 15(Spec2):R188-95, 2006.
Rapoport et al., *Proc. Natl. Acad. Sci. USA*, 99(9):6364-9, 2002.
Ringman et al., *Neurology*, 71(2):85-92, 2008.
Roberson et al., *Science*, 316(5825):750-4, 2007.
Roher et al., J. Neurochemistry, 61(5):1916-26, 1993.
Rojo et al., *PLoS One*, 6:e23111, 2011.
Santacruz et al., *Science*, 309(5733):476-81, 2005.
Schneider and Mandelkow, *Neurotherapeutics*, 5(3):443-57, 2008.
Sengupta et al., *Biochemistry*, 45(50):15111-9, 2006.
Shaw et al., *Ann. Neurol.*, 65(4):403-13, 2009.
Skoog et al., *Dement. Geriatr. Cogn. Disord.*, 15(3):169-76, 2003.
Songsivilai & Lachmann, *Clin. Exp. Immunol.*, 79:315-321, 1990.
Spires et al., *Am. J. Pathol.*, 168(5):1598-607, 2006.
Spires-Jones et al., *Trends Neurosci.*, 32(3):150-9, 2009.
Stewart and Young, In: *Solid Phase Peptide Synthesis*, 2d. ed., Pierce Chemical Co., 1984.
Tabaton et al., *Neurosci. Lett.*, 103(3):259-62, 1989.
Tam et al., *J. Am. Chem. Soc.*, 105:6442, 1983.
Teunissen et al., *Neurobiol. Aging*, 23(4):485-508, 2002.
Tigges et al., *J. Immunol.*, 156(10):3901-3910, 1996.
Trinczek et al., *Mol. Biol. Cell*, 6(12):1887-902, 1995.
Trojanowski et al., *Expert Opin. Pharmacother.*, 6(5):683-6, 2005.
Tsitsopoulos and Marklund, Front. Neurol. 4(Article 79):1-17, 2013.
Vandermeeren et al., *J. Neurochem.*, 61(5):1828-34, 1993.
Vaughan et al., *Nature Biotechnol.*, 16:535-539, 1998.
Vieira et al., *J. Neurochem.*, 103(2):736-48, 2007.
Vigo-Pelfrey et al., *Neurology*, 45(4):788-93, 1995.
Walsh and Selkoe, *Protein Pept. Lett.*, 11(3):213-28, 2004.
Walsh and Selkoe, *J. Neurochem.*, 101(5):1172-84, 2007.
Wiltfang et al., *World J. Biol. Psychiatry*, 6(2):69-84, 2005.
Wischik et al., *Proc. Natl. Acad. Sci. USA*, 93:11213-11218, 1996.
Wischik et al. *Proc. Natl. Acad. Sci. USA*, 85:4506-4510, 1988b.
Wischik et al., *Proc. Natl. Acad. Sci. USA*, 85:4884-4888, 1998a.
Wischik et al., In: *Microtubule-associated proteins: modifications in disease*, Avila et al. (Eds.), Harwood Academic Publishers, Amsterdam 185-241, 1997.
Yamazaki et al., *J. Neuropathol. Exp. Neurol.*, 64(10):839-46, 2005.
Yoshiyama et al., *Neuron.*, 53(3):337-51, 2007.
Zetterberg et al., *Neurosci. Lett.*, 352(1):67-9, 2003.
Zhang et al., *Proc. Natl. Acad. Sci. USA*, 102(1):227-31, 2005.

The invention claimed is:

1. A method for treating a concussion, comprising the step of administering a therapeutically effective amount of a Tau oligomer specific antibody that specifically binds Tau oligomers to a subject within 24 hours of the concussion, wherein a heavy chain variable region of the antibody comprises the amino acid sequence of SEQ ID NO: 11 and a light chain variable region of the antibody comprises the amino acid sequence of SEQ ID NO: 12.

2. The method of claim 1, wherein 0.1 mg to 10 mg of the Tau oligomer specific antibody is administered to the subject.

3. The method of claim 1, wherein the Tau oligomer specific antibody is administered into the blood or CSF.

4. The method of claim 1, wherein the subject is treated within 6 hr of the concussion.

5. The method of claim 1, wherein the subject is treated for at least 7 days after the concussion.

6. A method of identifying and treating a subject having a concussion comprising:
(i) contacting a biological sample from the subject suspected of having suffered said concussion with a Tau oligomer specific antibody that specifically binds Tau oligomers forming a complex with Tau oligomers and detecting the presence of a Tau oligomer specific antibody/Tau oligomer complex in the biological sample, thereby identifying a subject as having suffered said concussion, and
(ii) administering to the subject identified in step (i) as having said concussion a therapeutically effective amount of a Tau oligomer specific antibody that specifically binds Tau oligomers, wherein a heavy chain variable region of the antibody comprises the amino acid sequence of SEQ ID NO: 11 and a light chain variable region of the antibody comprises the amino acid sequence of SEQ ID NO: 12.

7. The method claim 6, wherein the biological sample comprises blood, plasma, platelets, saliva, cerebrospinal fluid (CSF), or brain tissue.

8. The method of claim 6, wherein the Tau oligomer specific antibody used in step (i) comprises a detectable agent.

9. The method of claim 8, wherein the detectable agent is a radioactive marker, a nucleic acid, a fluorescent label, or an enzymatic label.

* * * * *

SEQUENCE LISTING

```
<160> NUMBER OF SEQ ID NOS: 12

<210> SEQ ID NO 1
<211> LENGTH: 41
<212> TYPE: PRT
<213> ORGANISM: Artificial Sequence
<220> FEATURE:
<223> OTHER INFORMATION: synthetic peptide

<400> SEQUENCE: 1

Gly Lys His Gly Ala Gly Ala Ala Ala Gly Ala Val Val Gly Gly
1               5                   10                  15

Leu Gly Gly Tyr Gly Leu Gly Ser Ala Gly Ser Arg Pro Ile Ile His
                20                  25                  30

Phe Gly Ser Asp Tyr Glu Asp Arg Tyr
            35                  40

<210> SEQ ID NO 2
<211> LENGTH: 40
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15
```

```
Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 3
<211> LENGTH: 42
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 4
<211> LENGTH: 37
<212> TYPE: PRT
<213> ORGANISM: Homo sapiens

<400> SEQUENCE: 4

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 5
<211> LENGTH: 21
<212> TYPE: PRT
<213> ORGANISM: Homo sapiens

<400> SEQUENCE: 5

Lys Thr Asn Met Lys His Met Ala Gly Ala Ala Ala Ala Gly Ala Val
1               5                   10                  15

Val Gly Gly Leu Gly
            20

<210> SEQ ID NO 6
<211> LENGTH: 44
<212> TYPE: PRT
<213> ORGANISM: Artificial Sequence
<220> FEATURE:
<223> OTHER INFORMATION: Synthetic peptide

<400> SEQUENCE: 6

Lys Lys Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln Gln Gln
            20                  25                  30

Gln Gln Gln Gln Gln Gln Gln Gln Gln Lys Lys
        35                  40

<210> SEQ ID NO 7
<211> LENGTH: 147
<212> TYPE: PRT
<213> ORGANISM: Homo sapiens
```

<400> SEQUENCE: 7

```
Met Lys Ala Leu Ile Val Leu Gly Leu Val Leu Leu Ser Val Thr Val
1               5                   10                  15
Gln Gly Lys Val Phe Glu Arg Cys Glu Leu Ala Arg Thr Leu Lys Arg
            20                  25                  30
Leu Gly Met Asp Gly Tyr Arg Gly Ser Leu Ala Asn Trp Met Cys Leu
        35                  40                  45
Ala Lys Trp Glu Ser Gly Tyr Asn Thr Arg Ala Thr Asn Tyr Asn Ala
    50                  55                  60
Gly Asp Arg Ser Thr Asp Tyr Gly Ile Phe Gln Ile Asn Ser Arg Tyr
65                  70                  75                  80
Trp Cys Asn Asp Gly Lys Thr Pro Gly Ala Val Asn Ala Cys His Leu
                85                  90                  95
Ser Cys Ser Ala Leu Leu Gln Asp Asn Ile Ala Asp Ala Val Ala Cys
            100                 105                 110
Ala Lys Arg Val Val Arg Asp Pro Gln Gly Ile Arg Ala Trp Val Ala
        115                 120                 125
Trp Arg Asn Arg Cys Gln Asn Arg Asp Val Arg Gln Tyr Val Gln Gly
    130                 135                 140
Cys Gly Val
145
```

<210> SEQ ID NO 8
<211> LENGTH: 110
<212> TYPE: PRT
<213> ORGANISM: Homo sapiens

<400> SEQUENCE: 8

```
Met Ala Leu Trp Met Arg Leu Leu Pro Leu Leu Ala Leu Leu Ala Leu
1               5                   10                  15
Trp Gly Pro Asp Pro Ala Ala Ala Phe Val Asn Gln His Leu Cys Gly
            20                  25                  30
Ser His Leu Val Glu Ala Leu Tyr Leu Val Cys Gly Glu Arg Gly Phe
        35                  40                  45
Phe Tyr Thr Pro Lys Thr Arg Arg Glu Ala Glu Asp Leu Gln Val Gly
    50                  55                  60
Gln Val Glu Leu Gly Gly Gly Pro Gly Ala Gly Ser Leu Gln Pro Leu
65                  70                  75                  80
Ala Leu Glu Gly Ser Leu Gln Lys Arg Gly Ile Val Glu Gln Cys Cys
                85                  90                  95
Thr Ser Ile Cys Ser Leu Tyr Gln Leu Glu Asn Tyr Cys Asn
            100                 105                 110
```

<210> SEQ ID NO 9
<211> LENGTH: 147
<212> TYPE: PRT
<213> ORGANISM: Homo sapiens

<400> SEQUENCE: 9

```
Met Ala Ser His Arg Leu Leu Leu Leu Cys Leu Ala Gly Leu Val Phe
1               5                   10                  15
Val Ser Glu Ala Gly Pro Thr Gly Thr Gly Glu Ser Lys Cys Pro Leu
            20                  25                  30
Met Val Lys Val Leu Asp Ala Val Arg Gly Ser Pro Ala Ile Asn Val
        35                  40                  45
```

```
Ala Val His Val Phe Arg Lys Ala Ala Asp Asp Thr Trp Glu Pro Phe
 50                  55                  60
Ala Ser Gly Lys Thr Ser Glu Ser Gly Glu Leu His Gly Leu Thr Thr
 65                  70                  75                  80
Glu Glu Glu Phe Val Glu Gly Ile Tyr Lys Val Glu Ile Asp Thr Lys
                 85                  90                  95
Ser Tyr Trp Lys Ala Leu Gly Ile Ser Pro Phe His Glu His Ala Glu
                100                 105                 110
Val Val Phe Thr Ala Asn Asp Ser Gly Pro Arg Arg Tyr Thr Ile Ala
             115                 120                 125
Ala Leu Leu Ser Pro Tyr Ser Tyr Ser Thr Thr Ala Val Val Thr Asn
130                 135                 140
Pro Lys Glu
145

<210> SEQ ID NO 10
<211> LENGTH: 140
<212> TYPE: PRT
<213> ORGANISM: Homo sapiens

<400> SEQUENCE: 10

Met Asp Val Phe Met Lys Gly Leu Ser Lys Ala Lys Glu Gly Val Val
 1               5                  10                  15
Ala Ala Ala Glu Lys Thr Lys Gln Gly Val Ala Glu Ala Ala Gly Lys
                 20                  25                  30
Thr Lys Glu Gly Val Leu Tyr Val Gly Ser Lys Thr Lys Glu Gly Val
             35                  40                  45
Val His Gly Val Ala Thr Val Ala Glu Lys Thr Lys Glu Gln Val Thr
 50                  55                  60
Asn Val Gly Gly Ala Val Val Thr Gly Val Thr Ala Val Ala Gln Lys
 65                  70                  75                  80
Thr Val Glu Gly Ala Gly Ser Ile Ala Ala Ala Thr Gly Phe Val Lys
                 85                  90                  95
Lys Asp Gln Leu Gly Lys Asn Glu Glu Gly Ala Pro Gln Glu Gly Ile
                100                 105                 110
Leu Glu Asp Met Pro Val Asp Pro Asp Asn Glu Ala Tyr Glu Met Pro
             115                 120                 125
Ser Glu Glu Gly Tyr Gln Asp Tyr Glu Pro Glu Ala
130                 135                 140

<210> SEQ ID NO 11
<211> LENGTH: 120
<212> TYPE: PRT
<213> ORGANISM: Mus musculus

<400> SEQUENCE: 11

Glu Val Gln Leu Gln Gln Ser Gly Pro Glu Leu Val Lys Pro Gly Ala
 1               5                  10                  15
Ser Val Lys Met Ser Cys Lys Ala Ser Gly Tyr Thr Phe Thr Asp Tyr
                 20                  25                  30
Tyr Met Lys Trp Val Lys Gln Ser His Gly Lys Ser Leu Glu Trp Ile
             35                  40                  45
Gly Asp Ile Asn Pro Asn Asn Gly Asp Thr Phe Tyr Asn Gln Lys Phe
 50                  55                  60
Lys Gly Lys Ala Thr Leu Thr Val Asp Lys Ser Ser Ser Thr Ala Tyr
 65                  70                  75                  80
```

-continued

```
Met Gln Leu Asn Ser Leu Thr Ser Glu Asp Ser Ala Val Tyr Tyr Cys
            85                  90                  95

Ala Arg Gly Val Tyr Asp Gly Tyr Tyr Ala Met Asp Tyr Trp Gly Gln
           100                 105                 110

Gly Thr Ser Val Thr Val Ser Ser
           115             120

<210> SEQ ID NO 12
<211> LENGTH: 112
<212> TYPE: PRT
<213> ORGANISM: Mus musculus

<400> SEQUENCE: 12

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Lys
            100                 105                 110
```